(12) United States Patent
Homer

(10) Patent No.: US 12,383,427 B2
(45) Date of Patent: Aug. 12, 2025

(54) SYSTEMS AND METHODS FOR EYE IMAGING AND POSITION CONTROL

(71) Applicant: Stroma Medical Corporation, Irvine, CA (US)

(72) Inventor: Gregg Homer, Irvine, CA (US)

(73) Assignee: Stroma Medical Corporation, Irvine, CA (US)

( * ) Notice: Subject to any disclaimer, the term of this patent is extended or adjusted under 35 U.S.C. 154(b) by 0 days.

(21) Appl. No.: 18/607,209

(22) Filed: Mar. 15, 2024

(65) Prior Publication Data

US 2024/0216174 A1 Jul. 4, 2024

Related U.S. Application Data

(63) Continuation of application No. 17/571,102, filed on Jan. 7, 2022, now Pat. No. 11,931,295, which is a continuation of application No. 17/238,078, filed on Apr. 22, 2021, now Pat. No. 11,278,452.

(60) Provisional application No. 63/165,684, filed on Mar. 24, 2021.

(51) Int. Cl.
*A61F 9/008* (2006.01)
*G06V 40/18* (2022.01)

(52) U.S. Cl.
CPC ............ *A61F 9/008* (2013.01); *G06V 40/193* (2022.01); *A61F 2009/00846* (2013.01); *A61F 2009/00876* (2013.01); *A61F 2009/00878* (2013.01)

(58) Field of Classification Search
CPC ............ A61F 9/008; A61F 2009/00876; A61F 2009/00878

USPC .......................................................... 606/4–6
See application file for complete search history.

(56) References Cited

U.S. PATENT DOCUMENTS

| | | | | |
|---|---|---|---|---|
| 4,724,522 A | * | 2/1988 | Belgorod | A61F 9/008 606/5 |
| 8,206,379 B2 | * | 6/2012 | Homer | A61F 9/00817 606/4 |
| 2002/0181746 A1 | * | 12/2002 | Schwartz | A61B 3/14 382/117 |
| 2005/0049584 A1 | * | 3/2005 | Homer | A61F 9/00817 606/33 |
| 2007/0173793 A1 | * | 7/2007 | Rathjen | A61F 9/00825 606/4 |
| 2012/0265180 A1 | * | 10/2012 | Homer | A61F 9/00817 606/4 |
| 2013/0150836 A1 | * | 6/2013 | Bor | A61B 3/1225 606/4 |

(Continued)

FOREIGN PATENT DOCUMENTS

WO    WO-2019110855 A1  *  6/2019   ........... A61B 18/203

*Primary Examiner* — John R Downey
(74) *Attorney, Agent, or Firm* — Foley & Lardner LLP

(57) ABSTRACT

A method for altering an eye color of a patient with a color alteration procedure is disclosed that may include imaging the iris with an image sensor prior to the color alteration procedure to generate an image of the iris. A mapping of the iris may be generated from the image. The mapping may include a number of regions corresponding to varying absorption coefficients of a treatment wavelength in the stromal pigment of the iris. A laser system may be set, based on the mapping, to deliver laser light at a laser power sufficient to cause elimination of at least a portion of stromal pigment in the iris. The laser light may then be delivered with the laser system.

22 Claims, 12 Drawing Sheets

(56) References Cited

U.S. PATENT DOCUMENTS

| | | | |
|---|---|---|---|
| 2014/0148737 A1* | 5/2014 | Homer | A61H 23/00 |
| | | | 606/4 |
| 2017/0035608 A1* | 2/2017 | Boxer Wachler | A61B 3/135 |
| 2018/0036167 A1* | 2/2018 | Kenar | A61F 9/00821 |
| 2018/0121724 A1* | 5/2018 | Ovsiannikov | G06V 40/1312 |
| 2020/0046560 A1* | 2/2020 | Thyzel | A61F 9/00804 |
| 2020/0054489 A1* | 2/2020 | Thyzel | A61F 9/00802 |
| 2020/0093636 A1* | 3/2020 | Kenar | A61F 9/008 |

* cited by examiner

SYSTEMS AND METHODS FOR EYE IMAGING AND POSITION CONTROL

RELATED APPLICATION(S)

This application is a continuation of U.S. patent application Ser. No. 17/571,102, filed Jan. 7, 2022, which is a continuation of U.S. patent application Ser. No. 17/238,078, filed Apr. 22, 2021, now U.S. Pat. No. 11,278,452, which claims the benefit of priority of U.S. Provisional Application No. 63/165,684, filed Mar. 24, 2021, titled "Systems and Methods for Eye Imaging and Position Control." The content of the foregoing applications is hereby incorporated herein in its entirety by reference.

FIELD OF THE INVENTION

The invention relates to imaging and monitoring the eye for medical procedures related to changing the eye color of a patient.

BACKGROUND

The use of lasers for eye surgery has increased recently. However, while laser eye surgery is a known option for the correction of one or more vision problems such as near-sightedness (myopia), farsightedness (hyperopia), and astigmatism, little interest has been shown to operations other than those for correcting vision problems. For example, advancements in laser eye surgeries have focused on operations through which a laser may reshape a patient's cornea and have ignored other parts of a patient's eye and procedures therefor.

SUMMARY

In view of this, methods and systems are discussed herein for delivering laser light to an iris of a patient. In particular, the methods and systems discussed herein are for performing an eye color changing procedure through this delivery of laser light. For example, changing a person's eye color may be performed by delivering laser light to portions of the eye that are responsible for giving the eye its color (e.g., the iris).

To achieve this effect, the methods and systems must overcome several technical hurdles. For example, conventional systems provide no mechanism for the accurate delivery of light to large areas of the iris, and in particular accounting for local changes in the absorption of such laser light needed for the color alteration procedure described herein. Also, conventional systems do not account for iris tilt because such conventional systems are typically used only for very localized treatments (i.e., essentially a single point) where and iris tilt would not necessarily affect the outcome.

In view of these technical hurdles, the methods and systems discussed herein map the iris of the patient in order to characterize the extent of pigmentation that needs to be removed to change their eye color. This mapping allows determination of spatially varying absorption coefficients (of the laser light that is for treatment) in the iris. Also, to ensure that the laser light is accurately delivered to all regions of the eye needed for treatment, a scanning pattern for the delivery of the laser light is determined. Optical tracking of the eye is done during the procedure to ensure that laser light is delivered according to the scanning pattern. Another aspect that improves accurate delivery of laser light is monitoring the iris for unacceptable changes in tilt (e.g., due to patient motion).

These methods and systems provide numerous advantages over conventional methods for obtaining eye color changes such as colored contact lenses, corneal staining and tattooing, and prosthetic iris implants. For example, with colored contact lenses, such problems include: an unnatural appearance if blue or green contact lenses are used to make brown eyes appear blue or green; only a temporary color change; poor tolerance by about 50% of patients; risk of eye infection, corneal abrasion, and other eye disorders; and poor night vision because the clear center does not dilate with the pupil of the eye. Recent literature has also suggested that the pigments used in colored contact lenses may be released into the body after prolonged use. Other solutions are available, including corneal pigmentation and colored iris implants. Problems with corneal pigmentation include the same unnatural appearance and poor night vision as colored contact lenses, plus the added risks associated with an invasive surgical procedure. Problems with colored iris implants include all of the problems associated with corneal pigmentation, plus poor tolerance by 50% of patients within 24 hours and over 90% of patients within 1 year, and colored iris implants are far more surgically invasive, often resulting in glaucoma and loss of visual acuity. Neither corneal pigmentation nor colored iris implants have been approved for cosmetic use.

The methods and systems overcome these shortcomings of conventional systems by imaging the iris in order to generate a mapping that separates the iris into regions having particular absorption coefficients at the wavelength of the treatment laser. With such a determined mapping, specific laser settings may be applied to deliver laser power sufficient to eliminate stromal pigment in the iris. To ensure accurate delivery, first a scanning pattern (e.g., a spiral pattern between the pupil and the limbus) may be determined by the system. Then, during delivery, and optical tracking system may track the axial alignment of the eye and monitor for deviations from the scanning pattern. If a deviation is detected, then the power output of the laser system may be changed (e.g., reduced or halted). To further ensure proper eye position, rangefinding hardware and techniques may be used to determine and monitor the tilt of the iris during the procedure. If an unacceptable tilt is detected, a fixation target (e.g., point where the patient is looking) may be shifted by the system such that the patient looks in a different direction that compensates for the tilt.

In some aspects, a method for altering an eye color of a patient with a color alteration procedure may include imaging the iris with an image sensor prior to the color alteration procedure to generate an image of the iris. The system may generate a mapping of the iris from the image. The mapping may include a number of regions corresponding to varying absorption coefficients of a treatment wavelength in the stromal pigment of the iris. A laser system may be set, based on the mapping, to deliver laser light at a laser power sufficient to cause elimination of at least a portion of stromal pigment in the iris. The laser light may then be delivered with the laser system.

In some aspects, there may be another method that includes generating a scanning pattern for delivery of laser power to at least 50% of an iris. An optical tracking system may track the axial alignment of an eye of the patient during the color alteration procedure. The laser system may be set to deliver a first laser power to a location in the eye of the patient, the laser power sufficient to cause elimination of at least a portion of stromal pigment in an iris of the eye. The laser system may deliver laser light having this laser power to the eye according to the scanning pattern. The system may determine an amount that the eye is off axis based on the axial alignment. The amount may be compared a threshold and the laser system may be set to a second laser power when the amount equals or exceeds the threshold. The second laser power may be less than the first laser power. The laser system may deliver laser light to the eye at the second laser power and according to the scanning pattern.

In some aspects, a method may include generating a scanning pattern for the delivery of laser power to at least 50% of an iris. A rangefinder may be used in the tracking of the eye of the patient during the color alteration procedure. Utilizing the rangefinder, the system may determine an amount of tilt of the iris based on an optical tracking system interpreting optical data received from the eye of the patient. The system may compare the amount of tilt to a threshold amount. The system may then determine that the amount of tilt equals or exceeds the threshold amount. A fixation target characteristic of a laser system may be adjusted to compensate for the amount of tilt. The laser system may be set to deliver laser light having a laser power that will cause elimination of at least a portion of stromal pigment of the iris. The laser system may deliver, according to the scanning pattern, laser light having a laser power sufficient to cause elimination of at least a portion of stromal pigment of the iris.

In another interrelated aspect, a tangible, non-transitory, machine-readable medium storing instructions that, when executed by a data processing apparatus, causes the data processing apparatus to perform operations comprising those of any of the above method embodiments.

In yet another interrelated aspect, a system may include one or more processors and memory storing instructions that, when executed by the processors, cause the processors to effectuate operations comprising those of any of the above method embodiments.

Various other aspects, features, and advantages of the invention will be apparent through the detailed description of the invention and the drawings attached hereto. It is also to be understood that both the foregoing general description and the following detailed description are examples and not restrictive of the scope of the invention. As used in the specification and in the claims, the singular forms of "a," "an," and "the" include plural referents unless the context clearly dictates otherwise. In addition, as used in the specification and the claims, the term "or" means "and/or" unless the context clearly dictates otherwise. Additionally, as used in the specification "a portion," refers to a part of, or the entirety of (i.e., the entire portion), a given item (e.g., data) unless the context clearly dictates otherwise.

DETAILED DESCRIPTION OF THE DRAWINGS

In the following description, for the purposes of explanation, numerous specific details are set forth in order to provide a thorough understanding of the embodiments of the invention. It will be appreciated, however, by those having skill in the art, that the embodiments of the invention may be practiced without these specific details or with an equivalent arrangement. In other cases, well-known structures and devices are shown in block diagram form in order to avoid unnecessarily obscuring the embodiments of the invention.

The present disclosure provides improved methods and systems for facilitating medical procedures to change the eye color of a patient. Such medical procedures may involve delivering laser power to portions of the eye such that a biological reaction occurs that alters the pigment structure of the eye and thereby changes its color. Determining the proper laser power to use based on the needs of the procedure, safety to the patient, variations from patient to patient, and variations from treatment to treatment (for a multistage treatment) may be critical to a successful outcome.

Figure 1:
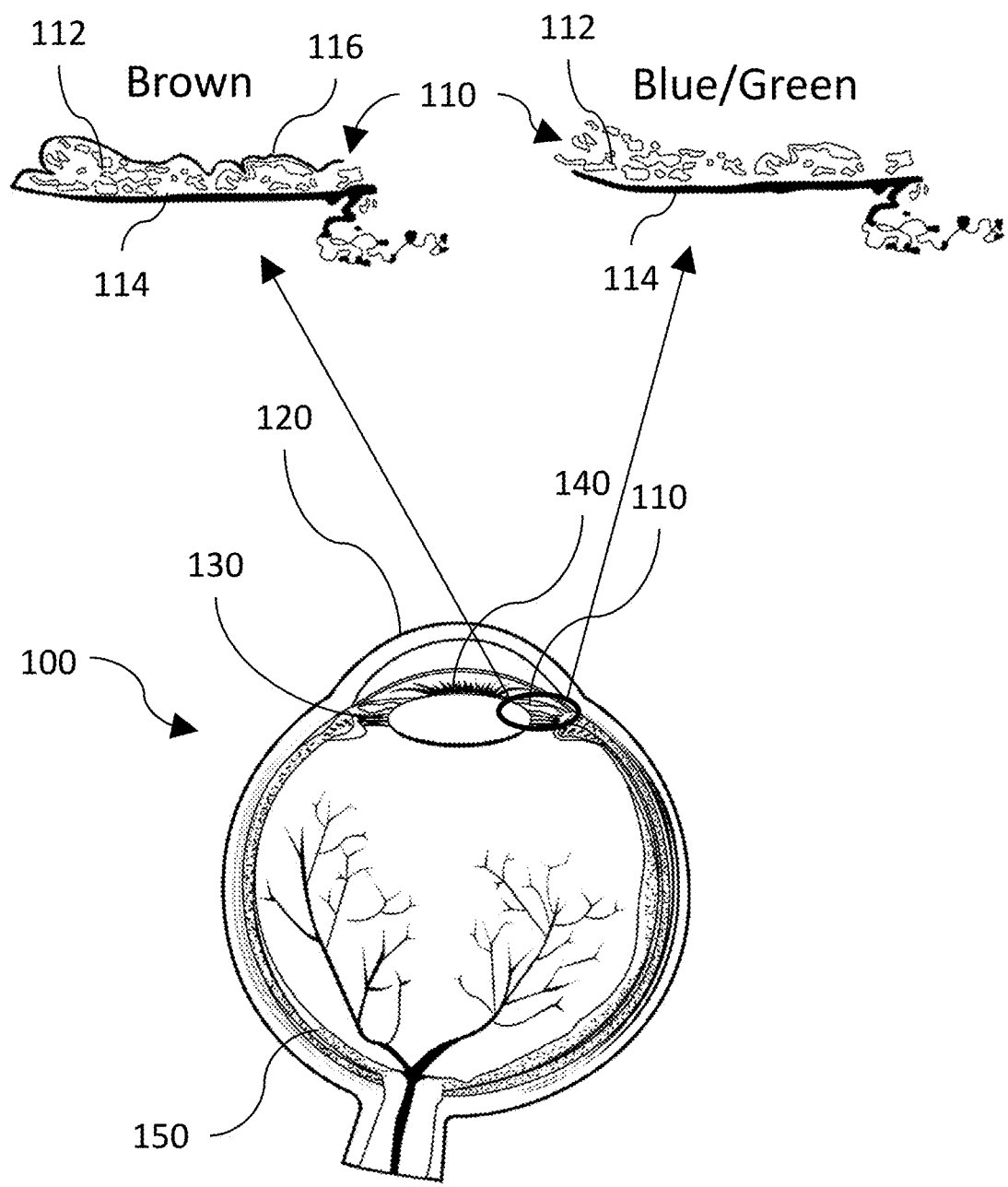
FIG. 1 shows a simplified diagram of the eye and iris.

Before describing the color alteration procedure, which is applicable to many embodiments of the present disclosure, a brief overview of the anatomy of the eye is provided. As shown in FIG. 1, eye 100 is composed of several anatomical structures, a few of which are discussed below. Central to the present disclosure, the iris 110 is responsible for the color of the eye. Other portions of the eye include, for example, cornea 120, lens 130, pupil 140, and retina 150. While care should be taken to avoid damaging any part of the eye, in the practice of laser safety, special precautions should be taken to avoid directing unwanted laser light through the pupil and into the lens as this part of the eye naturally focuses light onto the retina. Such focusing of already intense laser light may result in injury to the retinal nerves.

Shown in the insets above the eye are two examples of irises. The example on the left is a depiction of an iris 110 in a person with brown eyes. The example on the right depicts an iris 110 of a person with blue or green eyes. The perceived color is due to light reaching the eye being separated into its component wavelengths by stromal fibers in the middle region of the iris—referred to as the iris stroma 112. The separation is similar to the separation exhibited when light passes through a prism. In both cases, the iris has a posterior surface 114 that contains a fairly thick (several cells deep) layer of pigmentation that primarily absorbs visible light wavelengths longer than blue or green. However, in the example on the left for a person with brown eyes, there is an additional anterior surface that contains brown pigment, herein referred to as "stromal pigment" 116. The brown stromal pigment gives the eye a brown color. Eyes without the stromal pigment reflect mostly blue or green light as described above, giving the eye a blue or green color.

A brief summary of a color alteration procedure as referenced herein is provided. Laser light may be delivered to the stromal pigment to cause an increase in temperature of the stromal pigment. This process may be repeated several times to repeatedly raise and lower the temperature of the stromal pigment. This raising and lowering of the temperature causes the body to deploy macrophages (part of the body's natural immune response) to the stromal layer. These macrophages then remove a portion of the stromal pigment responsible for giving the eye its brown color. Repeated procedures may be performed to provide varying degrees of color change to make the eye appear a deeper blue/green. The delivery of the laser light may be in a scanning pattern (e.g., a spiral pattern surrounding the pupil or a raster pattern avoiding the pupil) to deliver the treatment to the entire iris.

Figure 2:
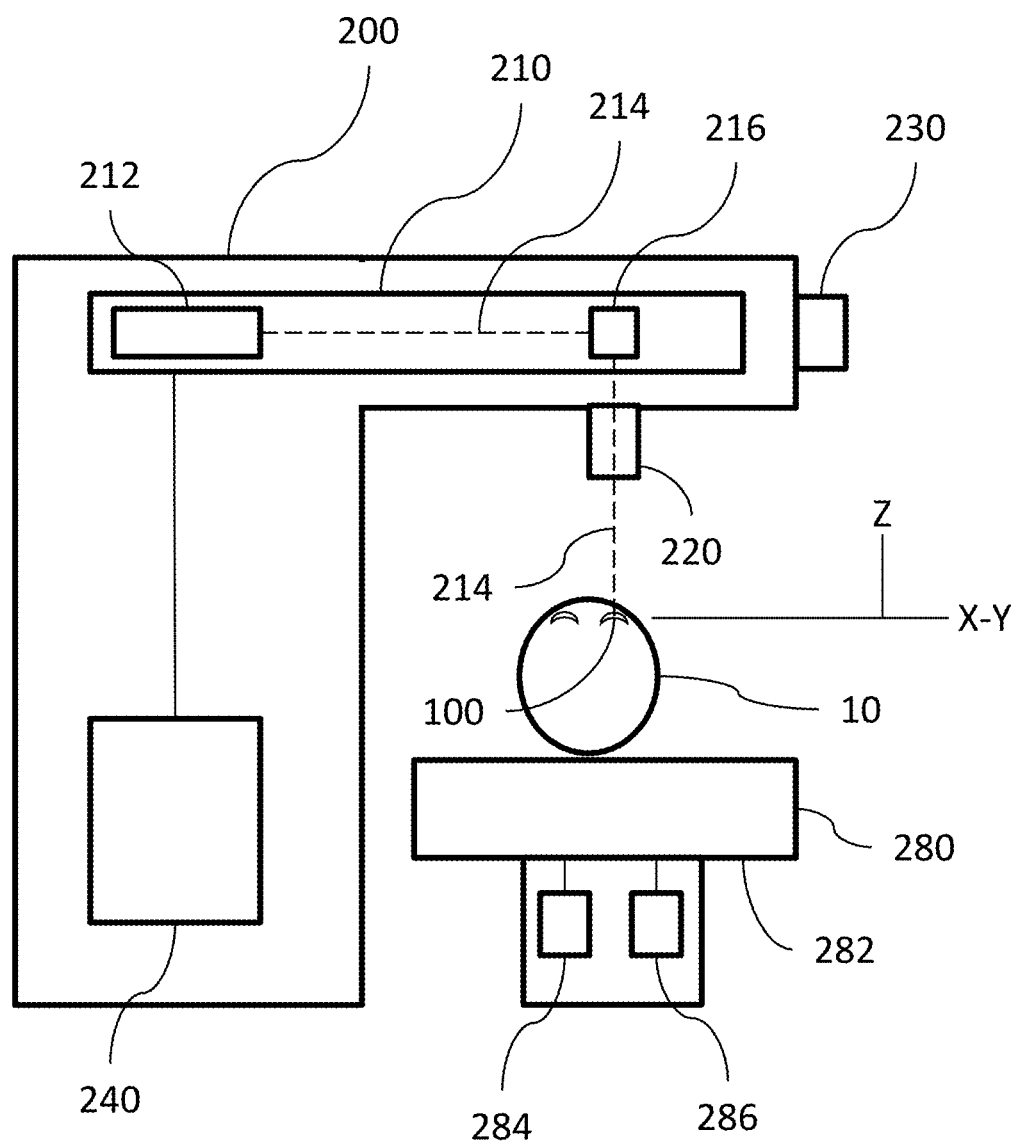
FIG. 2 shows a simplified diagram of a laser system and patient positioning system in accordance with one or more embodiments.

FIG. 2 shows a simplified diagram of a laser system and patient positioning system in accordance with one or more embodiments. One embodiment of the overall system 200 may include the laser system 210 and a patient positioning system 280. The head of patient 10 (with eyes 100) is shown supported by the patient positioning system in a location suitable for the color alteration procedure. The laser system may include the laser head 212 which provides laser light 214. The laser head may include components to generate laser light at varying wavelengths, for example, at 1064 nm or 532 nm (Nd:YLF or Nd:YAG). Exemplary pulse widths may be in the 5-300 ns with repetition rates of 5-300 kHz and an $M^2 \leq 1.2$.

The laser head may include an energy source (aka a pump or pump source), a gain medium, and two or more mirrors that form an optical resonator. Exemplary energy sources include: electrical discharges; flashlamps; arc lamps; output from another laser; and chemical reactions. Exemplary gain media include: liquids (e.g., dyes comprising chemical solvents and chemical dyes); gases (e.g., carbon dioxide, argon, krypton, and helium-neon); solids (e.g., crystals and glasses, such as yttrium-aluminum garnet, yttrium lithium fluoride, sapphire, titanium-sapphire, lithium strontium aluminum fluoride, yttrium lithium fluoride, neodymium glass, and erbium glass), which may be doped with an impurity (e.g., chromium, neodymium, erbium, or titanium ions) and may be pumped by flashlamps or output from another laser; and semiconductors, with uniform or differing dopant distribution (e.g., laser diode).

Embodiments of the laser head may include an optical frequency multiplier (e.g., a frequency doubler and sum-frequency generator), where the laser output frequency is increased by passing it through a non-linear crystal or other material. The benefit of an optical frequency multiplier is that it increases the range of frequencies/wavelengths available from a given gain medium. The non-linear material may be inserted into the optical resonator for one-step frequency multiplication, or the fundamental (i.e., non-multiplied) output beam may be passed through the non-linear material after leaving the optical resonator for two-step frequency multiplication. Exemplary non-linear materials for frequency doubling may include: lithium niobate, lithium tantalate, potassium titanyl phosphate, or lithium triborate. Two-step frequency tripling is typically performed by frequency doubling a fraction of the fundamental output beam in a first step. The doubled fraction of the fundamental beam and the non-doubled remainder of the fundamental beam are then coupled into a second non-linear frequency tripling material in a second step for sum-frequency mixing. Exemplary non-linear materials for frequency tripling may include potassium dihydrogen phosphate.

One combination of gain medium and optical frequency multiplier is Nd:YAG with a frequency doubler. The natural harmonic of a laser beam generated by an Nd:YAG gain medium is a wavelength of 1,064 nm, which is then halved to 532 nm by the frequency doubler. This wavelength may be utilized as: (a) it falls within the visible light spectrum (i.e., green), thereby passing through the clear cornea with little or no absorption; (b) it has a high absorption coefficient in stromal pigment, thereby effecting selective photothermolysis in the anterior stromal pigment of the iris; and (c) the wavelength is relatively short, thereby limiting the depth of penetration and avoiding unwanted damage to the IPE. Any other combination of gain media and optical frequency multiplication that meets these three criteria is also may also be implemented in some embodiments.

Laser pulse widths may be in the nanosecond range (i.e., from below 1 nanosecond to 1 microsecond) and the pulse repetition rate may be in the kilohertz range (i.e., from below 1 kHz to 1 MHZ). Some embodiments may have a pulse width between 5 ns and 300 ns, which may provide improved pigment denaturation. Q-switching may be utilized as a preferred pulsing method as it tends to be optimally suited to the nanosecond pulse width. Some embodiments include active Q-switching with a modulator device.

As used herein, "laser" means any device capable of generating a beam of optical radiation, whether in the infrared, visible light, or ultraviolet light spectrum. The term "laser" is not intended to restrict: (a) the properties of the optical radiation in terms of monochromaticity or coherence (e.g., divergence or directionality); (b) whether the radiation is continuous or pulsed; (c) if pulsed, the specific pulse width (e.g., zeptosecond attosecond, femtosecond, picosecond, nanosecond, millisecond, or microsecond); (d) the repetition rate; (e) the laser power; (f) the wavelength or frequency of the beam; (g) the number of wavelengths or frequencies, i.e., single v. multi-frequency output (e.g., intense pulsed light); (h) the number of beams, i.e., single v. multiple beams (e.g., splitting of a single beam or generating multiple beams from multiple lasers); or (i) the gain medium.

As used herein, "laser power" may mean either $W/cm^2$ or $J/cm^2$, depending on the context—as they are related by the exposure time. The MPE may be expressed in either of those units. For example, MPE may include the maximum level of laser radiation to which a fundus may be exposed without hazardous effects or biological changes in the eye.

Accordingly, when the specification refers to a laser power in terms of an MPE, the exact value of the laser power depends on, among other things, the beam spot size, pulse duration, or wavelength, and whether the laser is pulsed or continuous, etc. Thus, the determination of the MPE provides a basis for the skilled person to determine the laser power in the various embodiments disclosed herein.

As used herein, when referring to "reducing," "lowering," "less," etc., in the context of adjusting the laser power, this is understood to mean that the laser system may reduce the laser power from a current value to a lower (nonzero) value while still delivering laser light in some respect. These definitions also include redirecting the laser beam (e.g., to a beam dump) such that the delivered laser power is reduced.

These definitions also include turning off the laser system (i.e., lowering the laser power to zero). Lastly, reducing the laser power may also include performing any of the above in a repetitive fashion thereby lowering the duty cycle of the laser beam or performing any combination of the above in an intermittent fashion.

Galvos systems 216 (also referred to as the x-y beam guidance system) may be included in the laser system and may include adjustable mirrors to provide a means of delivering the laser light to various locations on an X-Y plane (typically the plane of the iris where the laser light usually focused). Further implementations of the laser system may include, for example rangefinders and/or optical tracking systems, which may include cameras to determine an X-Y deviation of the center of the eye relative to the optical axis of the laser system.

In some embodiments, the x-y beam guidance system may scan the beam spot about the iris surface. The scanning parameters may include the size, shape, and position of the target region, the line and spot separation between each beam spot, and the predetermined scan pattern. The computer imaging software may determine the size, shape, and position of the target region based upon iris images captured by the x-y imaging system and transmitted to the computer for processing. Once processed, the size, shape, and position data may be transmitted to the scanning program to drive the x-y beam guidance system. New iris images may be captured at predetermined intervals and transmitted to the computer for processing throughout the procedure. Captured images are compared, and if they indicate a change in iris position, the computer imaging software calculates the x-y deltas and transmits the shift coordinates to the scanning program, which in turn executes the shift in the scanning position. In some procedures, a topical cholinergic agonist such as pilocarpine hydrochloride ophthalmic solution 2% (e.g., Isopto Carpine 2% from Alcon, Geneva, Switzerland) may be instilled in the target eye prior to treatment to constrict the pupil, flatten out the iris surface, and mitigate changes in the iris size and shape during the procedure. The line and spot separation between each beam spot may be predetermined and programmed into the scanning program prior to treatment. In some cases, the spot and line separation place each beam spot tangent to the others throughout the target region. The scan pattern may be raster (including slow-x/fast-y and slow-y/fast-x), spiral (including limbus to pupil and pupil to limbus), vector, and Lissajous scans.

In one embodiment, the x-y beam guidance system may scan the beam spot about the iris surface by means of controlled deflection of the laser beam. Embodiments utilizing beam steering in two dimensions may drive the beam spot about the two-dimensional surface of the iris. Beam motion may be periodic (e.g., as in barcode scanners and resonant galvanometer scanners) or freely addressable (e.g., as in servo-controlled galvanometer scanners). Exemplary beam steering in two dimensions may include: rotating one mirror along two axes (e.g., one mirror scans in one dimension along one row and then shifts to scan in one dimension along an adjacent); and reflecting the laser beam onto two closely spaced mirrors mounted on orthogonal axes.

There are numerous methods for controlled beam deflection, both mechanical and non-mechanical. Exemplary non-mechanical methods may include: steerable electro-evanescent optical refractor or SEEOR; electro-optical beam modulation; and acousto-optic beam deflection. Exemplary mechanical methods may include: nanopositioning using a piezo-translation stage; the micro-electromechanical system or MEMS controllable microlens array; and controlled deflection devices. Mechanically controlled deflection devices may include: motion controllers (e.g., motors, galvanometers, piezoclectric actuators, and magnetostrictive actuators); optical elements (e.g., mirrors, lenses, and prisms), affixed to motion controllers; and driver boards (aka servos) or similar devices to manage the motion controllers. The optical elements may have a variety of sizes, thicknesses, surface qualities, shapes, and optical coatings, the selection of which depends upon the beam diameter, wavelength, power, target region size and shape, and speed requirements. Some embodiments may utilize optical elements that are flat or polygonal mirrors. An embodiment of the motion controller may include a galvanometer, including a rotor and stator (to manage torque efficiency) and a position detector (PD) (to manage system performance). An exemplary PD may include one or more illumination diodes, masks, and photodetectors. Driver boards may be analog or digital. Scan motion control might also comprise one or more rotary encoders and control electronics that provide the suitable electric current to the motion controller to achieve a desired angle or phase. The installed scanning program disclosed above may be configured to collect measured scan and target region data.

The x-y beam guidance system may apply the laser spot to all or any portion of the anterior iris surface. Treated fractions of the anterior iris surface may include the following (which are inclusive and do not take into account any spared tissue due to line and/or spot separations): greater than ¼; greater than 30%; greater than ⅓; greater than ½; and greater than ¾.

The system can include one or types of rangefinding apparatuses to measure the Z distance from a reference point to the target (e.g., the iris surface). As used herein, the Z direction is taken to be the vertical direction, perpendicular to the X-Y plane (e.g., the iris surface). A component referred to herein as optical exit 220 may be provided to allow the exiting of laser light to reach the eye. Optical exit 220 may include windows, lenses (e.g., dichroic lenses), mirrors, shutters, or other optical components. In some implementations, the system may include platform control 230, which may be configured to provide coarse adjustment (manually or automatic computer-controlled) in the X, Y, or Z directions. The platform control 230 may also be configured to perform fine adjustments similar to the above, with such fine adjustments implemented by computer control. Also included in some implementations are control computer and power supplies, depicted by element 240 in FIG. 1. Alternatively, control computers or electronics and some or all of the needed power supplies need not be contained in the system 200 as depicted in FIG. 1, but may be distributed in other locations or networked to be operatively connected to the laser system. Examples of rangefinding apparatuses may include systems that perform triangulation, time-of-flight measurements, etc., with one specific example being an optical coherence tomography system. Further discussion of rangefinding and/or tracking apparatuses is provide throughout the application.

Patient positioning system 280 is shown in the simplified diagram as containing patient support 282. Examples of patient support may include a flatbed, recliner, couch, head or neck brace, etc. Control of the patient positioning system may be realized by, for example, X-Y actuator 284 and/or Z actuator 286, which may be configured to move the patient in the respective directions for optimal alignment with the delivered laser light.

Included in the present disclosure are methods for the improved delivery of laser light for performing the above-described color alteration procedure. One way to deliver a consistent and clinically safe amount of laser light that is still effective for performing the color alteration procedure may include the system determining laser criteria in terms of this safe amount.

The laser settings used for treatment as described in the present disclosure may be determined by the system based on a number of parameters. One parameter may be the maximum permissible radiative exposure limit at the fundus plane of the eye ("MPE"). The MPE is a safety parameter to protect the retina from injury. A second parameter may be the minimum required radiative exposure at the iris plane of the eye ("MRE"). The MRE is an efficacy parameter to ensure that a threshold radiative exposure value is achieved for stromal pigment elimination.

The MPE may be obtained according to international safety standards. Examples of such standards include (a) American National Standard for Ophthalmics—Light Hazard Protection for Ophthalmic Instruments (ANSI Z80.36-2021), published by the American National Standards Institute (New York, NY, USA) in 2021, and (b) Safety of Laser Products—Part 1: Equipment Classification and Requirements (IEC 60825-1), published by the International Electrotechnical Commission (Geneva, Switzerland) in 2014.

In some implementations, the wavelength ($\lambda$) of the laser radiation may be between 305 nm and 1350 nm, inclusive, and the single pulse width (t) of the laser radiation may be between 100 fs and 5000 s, inclusive. To provide one example, which may change based on updating of the above-described standards, within these $=$ and t ranges the MPE may be calculated as follows:

(a) If 100 fs<t≤10 ps; and
   (i) $\lambda$=700 nm, then MPE=8.0 mJ/cm$^2$.
   (ii) $\lambda \neq$700 nm, then MPE=8.0 mJ/cm$^2$ divided R($\lambda$), where R($\lambda$) is defined as the thermal hazard weighting function for a given $\lambda$ in Appendix 1.

(b) If 10 ps<t<<3 µs; and
   (i) $\lambda$=700 nm, then MPE=20.0 mJ/cm$^2$
   (ii) $\lambda \neq$700 nm, then MPE=20.0 mJ/cm$^2$ divided by R($\lambda$).

(c) If 3 µs≤t<5000 s, then MPE is given by the following Equation (1):

$$\frac{\left(\frac{10}{d_r} \cdot t^{0.75}\right) \frac{J}{cm^2}}{R(\lambda)}$$

where
t is the single pulse width (in seconds);
$d_r$ is the minimum retinal image diameter (in mm) of the laser beam in the standard eye; and if $d_r \geq d_r(\text{max})$, then $d_r = d_r(\text{max})$, where if 3 µs ≤ t < 0.25 s, then $d_r(\text{max}) = 3.4 \cdot t^{0.5}$ mm;

if t ≥ 0.25 s, then $d_r(\text{max}) = 1.7$ mm; and if $d_r(\text{max}) \leq 0.03$ mm, $d_r = 0.03$ mm.

The MRE is the minimum radiative exposure value capable of denaturing the pigment granules (melanosomes) within the pigment cells (melanocytes) located primarily along the anterior surface of the iris of the eye and secondarily and at lesser density within the stromal fibers of the iris of the eye. Denaturation of these pigment granules occurs at or about the temperature at which microbubbles first occur on the surfaces of the granules. These microbubbles typically occur at approximately 120° C. These microbubbles need not be maintained for a long duration or recreated multiple times. A single exposure may be sufficient to induce denaturation of the granule. Once a critical mass of these granules is denatured within a given cell, the cell will die off, signaling macrophages residing in and about the iris to digest the cell and remove it through the vasculature of the iris.

Real-time detection of the melanosome surface microbubbles may be achieved by the system monitoring the anterior iris surface optically or acoustically during treatment. One embodiment of an optical microbubble monitoring system may include a video microscope using a standard 40× microscope objective through which fast flash photographs may be taken by a high-speed image device (such as the 4 Quik E ICCD nanosecond high-speed camera from Stanford Computer Optics, Berkeley, CAS, USA), a frame grabber (such as the Cyton-CXP4 from BitFlow, Woburn, MA, USA), and a 3-5 ns flash illumination source (such as the VSL-337ND-S Pulsed Nitrogen Laser from Spectra-Physics, Santa Clara, CA, USA). Another example of an optical microbubble monitoring system captures the increased light reflection from the generated bubble-water interface using confocal imaging to a photomultiplier (such as the H7827-001 photosensor module from Hamamatsu, Hamamatsu City, Japan). The system may then record the output data using a transient recorder (such as the TR40-16 bit-3U from Licel GmbH, Berlin, Germany) and transfer the recorded data to a computer (such as the TPC-2230 from NI, Austin, TX, USA) for processing and analysis. Similarly, the system may include an electron microscopy system configured to perform electron microscopy on the iris during a treatment session (e.g., real-time and in-situ). For example, an electron microscopy system (such as the Quantax 70 (Bruker AXS Microanalysis GmbH, Berlin, Germany) may be configured to image and detect microbubbles as described above.

One embodiment of an acoustic microbubble monitoring system may include a hydrophone (such as the HFO-690 optical fiber hydrophone from Onda, Sunnyvale, CA, USA). Again, the output data may be recorded using a transient recorder (such as the TR40-16 bit-3U from Licel GmbH, Berlin, Germany) and transferred to a computer (such as the TPC-2230 from NI, Austin, TX, USA) for processing and analysis.

The descriptions of exemplary laser powers that may be delivered are used to cause biological actions that result in the desired alteration in eye color. Accordingly, in some implementations, the laser power may be sufficient to cause a concurrent temperature change in the stroma pigment, which then causes macrophages in the iris to remove at least a portion of the stromal pigment. In this way, monitoring of the iris temperature may be performed by the system to determine the MRE (e.g., detecting the exposure at which microbubbles begin to form). In some specific embodiments, the laser power may be at least 20 times the maximum permissible exposure such that a reduction of the laser power to below 20 times the maximum permissible exposure does not cause loosening denaturing of the stromal pigment and the resultant change in eye color. To facilitate delivery of laser power to cause sufficient temperature changes in the stromal pigment, some methods may include determining, with a temperature sensor, a temperature of at least a portion of the iris that contains stromal pigment. In some embodiments, the temperature sensor may be of a type non-invasive to the iris. Examples of temperature sensors may include more direct temperature sensors such as passive infrared detectors that image the eye or more indirect temperature sensors utilizing acoustical monitoring that detects acoustical signals (sounds or pressure waves) indicative of microbubble formation (e.g., as expected to occur around 120° C. and thus an approximation of the temperature crossing that threshold). Heat transfer from within the iris may manifest itself as local heating at the surface of the eye. Computer modeling of predicted or a priori heat patterns may be associated with the measured heat pattern to derive a heat pattern at the activated stromal pigment. For example, with an implementation that utilizes an infrared imaging system, the received infrared radiation may be converted by the imaging system, or a connected computer receiving data from such, to a local temperature in the iris. Such a conversion may be performed using a blackbody approximation or other similar methods.

One factor complicating ascertainment of the MRE is that it may vary from one melanosome to the next based upon the absorption coefficient between the wavelength of the radiative energy and the color value and/or density of the melanosome. If the MRE is too low for a given melanosome, no microbubbles will form, the melanosome will not be denatured, and its melanocyte will not be digested and eliminated. Conversely, if the MRE is too high for a given melanosome, too much heat will be generated within the melanocyte, ablating the melanocytes and causing them to burst, releasing the melanosomes into the anterior chamber of the eye, potentially causing inflammation in the adjacent tissues and its associated adverse conditions. The MRE for a given melanosome must therefore be appropriate for each melanosome.

By way of example, a 532 nm wavelength may be generated by the laser system to treat an iris with melanosomes having three color values/densities: tan, medium brown, and dark brown. The MRE required to denature the dark brown melanosomes will be lower than the MRE required to denature the tan and medium brown melanosomes (because the absorption coefficient between the wavelength and the dark brown color value/density is higher). The MRE required to denature the medium brown melanosomes will be higher than the MRE required to denature the dark brown melanosomes (because the absorption coefficient between the wavelength and the medium brown color value/density is lower), and the MRE required to denature the medium brown melanosomes will be lower than the MRE required to treat the tan melanosomes (because the absorption coefficient between the wavelength and the medium brown color value/density is higher). And the MRE required to denature the tan melanosomes will be higher than the MRE required to denature the medium and dark brown melanosomes (because the absorption coefficient between the wavelength and the tan color value/density is lower). Denaturation of the stromal melanosomes of this iris will therefore require three different MREs.

Real-time detection of the melanosome surface microbubbles will inform each MRE in the above example. In one embodiment, the initial radiant exposure value is too low to induce microbubbles but is gradually increased until microbubbles are first detected. Let us call this "MRE I." The entire iris may then be treated using MRE I. This treatment will denature the dark brown melanosomes, and their melanocytes will be digested and eliminated over the next 3-4 weeks. At 4 weeks, the treatment protocol may be repeated. Because most or all of the dark brown melanosomes are eliminated, the first microbubbles will be detected at a higher radiant exposure value. Let us call this "MRE II." The entire iris may then be treated using MRE II. This treatment will denature the medium brown melanosomes, and their melanocytes will be digested and eliminated over the next 3-4 weeks. At 4 weeks, the treatment protocol may be repeated. Because most or all of the medium brown melanosomes are eliminated, the first microbubbles will be detected at a higher radiant exposure value. Let us call this "MRE III." The entire iris may then be treated using MRE III. This treatment will denature the tan melanosomes, and their melanocytes will be digested and eliminated over the next 3-4 weeks. If stromal melanocytes remain on the anterior iris surface, treatment may be repeated using MRE III.

If melanocytes remain within the iris stroma, they will absorb the backscattered blue or green light, making the grey of the stroma fibers more visible, producing a grey-blue or grey-green perceived iris color. Many patients are satisfied with this perceived color because the grey increases the color value of the eye, making them appear brighter. For those patients who prefer a more saturated blue or green color hue, the treatment may be repeated at the MRE III value, but with the laser beam waist shifted from the anterior iris surface to the interior stroma. This treatment will denature the melanocytes remaining within the iris stroma and eliminate or reduce the absorption of the backscattered blue or green light.

Highly sensitive methods and devices should be used for real-time microbubble detection. If detection is not sufficiently sensitive, and the microbubbles are not detected when they first appear, the radiant energy will be too high, causing ablation of the melanocytes and inflammation of anterior chamber tissues. The radiative exposure value for two laser iris procedures, "argon laser trabeculoplasty" ("ALT") and "selective laser trabeculoplasty" ("SLT"), is established by increasing the radiative energy until "champaign bubbles" are visible on the trabecular meshwork ("TM"), and then reduced slightly. These champaign bubbles are substantially larger than microbubbles, and they occur at a higher radiative exposure value. Because the ALT and SLT procedures are limited to scattered clusters of melanocytes originating from the iris pigment epithelium and lodged in the TM, delivery of an excessive radiative exposure value and ablation of these clusters is unlikely to release a sufficient quantity of melanosomes to cause serious inflammation or injury to the eye. Here, however, an excessive radiative exposure value and ablation of the stromal melanocytes can cause severe inflammation and could in theory cause long-term injury.

In one implementation, the following exemplary MRE ranges are given for each of the following melanosome color values/densities, where $\lambda=532$ nm, t=11.475 ns, the pulse repetition rate (prr)=135 kHz, and the incidence angle of the beam to the iris plane $(\theta_i)=0°$:

| MRE | Color Value/Density | MRE Range (mJ/cm$^2$) |
| --- | --- | --- |
| MRE I | Dark brown | 250-400 |
| MRE II | Medium brown | 550-650 |
| MRE III | Tan | 750-850 |

The above MRE ranges are specific to the laser radiation parameters described above, but may vary with changes in these parameters. The methods for determining the MPE, however, take the relevant parameters into account. Therefore, the MRE ranges will necessarily take these parameters into account if they are expressed as multiples of the MPE.

Using $R(\lambda)=2.10$ as the weighting factor given in Appendix 1 for $\lambda=532$ nm and $t=11.475$ ns, the MPE is 9.52 mJ/cm$^2$ (i.e., 20 mJ/cm$^2$/2.10). The MPE for the parameters used in the Exemplary Embodiment is therefore approximately 9.52 mJ/cm$^2$, and the MREs can be expressed by the following MPE multiples:

| MRE | MRE Range (mJ/cm$^2$) | MPE Multiple Range |
| --- | --- | --- |
| MRE I | 250-400 | 26.26-42.02 × MPE |
| MRE II | 550-650 | 57.77-68.28 × MPE |
| MRE III | 750-850 | 78.78-89.29 × MPE |

As illustrated by the above MPE multiples, the MREs are considerably higher than the MPE. The iris is far less sensitive to excessive radiative exposure, and the consequences of excessive radiative iris exposure are not as severe in any case. In addition, the melanocytes of the fundus (known as the "retinal pigment epithelium" or "RPE") are generally darker and denser than those of the anterior iris, so the absorption coefficients in the fundus are higher. Also, the lens will focus the beam onto the fundus, thereby increasing its energy density at the fundus. Nevertheless, the MREs must be achieved without exceeding the MPEs in case the beam accidentally passes through the pupil (or any other opening in the iris) to the fundus.

In most cases, pulses fired through the pupil and focused onto the fundus will represent a "pulse train." A pulse train occurs where two or more successive pulses fully or partially overlap onto the target plane. This is particularly true in the case of the preferred embodiment, where $\theta_i$ remains at or about 0° throughout the procedure. Even if the beam is moving during the procedure (as assumed), the crystalline lens will focus the pulses onto a single spot on the fundus.

Regardless of the specific iris scan pattern, the beam path will likely cycle between the pupil and the iris. The iris cycles will likely be of sufficient duration to separate the pupil cycles into independent pulse trains. Under these circumstances, the maximum number of pulses in the pulse train (given by N below) will be the diameter of the pre-operative pupil (in mm), divided by the spot separation (in mm). If the operator follows the preferred embodiment below of triple pre-operative dosing with Pilocarpine 2%, the pupil diameter should be ≤1.0 mm. If the spot diameter (at 1/e$^2$), for example, were 0.05 mm, and the spot separation were 0.05 mm (i.e., the spots are tangent), then N=1/0.05=20 pulses. Unless otherwise indicated, 1/e$^2$ is used to define the beam waist.

Where pulses are members of a pulse train, the MPE calculated above may also be multiplied by an attenuation factor, $C_P$, calculated as follows:

(a) If t≥3 μs, then $C_P$ is given by the following Equation (2):

$$C_P = \left(\frac{dr(t)}{dr(T)}\right) \cdot N^{-0.25} \cdot D^{-0.75} \cdot 0.7^{(1-D)}$$

where

N is the number of pulses in the pulse train;
t is the single pulse width (in seconds);
tp is the period of a single pulse (in seconds);
T is the duration of the pulse train (in seconds), equal to the value N×tp;

D is the duty cycle of the pulse, equal to t/tp;
dr(t) is the dr (in mm) for a pulse of duration t, up to a maximum of dr(t)=3.4t$^{0.5}$; and
dr(T) is the dr (in mm) for T, up to a maximum of dr(T)=3.4 T$^{0.5}$.

(b) If t<3 μs, then $C_P$ is given by the following Equation (3):

$$C_p = \frac{10}{d_r(T)} \cdot t^{0.75} \cdot D^{-0.75} \cdot N^{-0.25} \cdot \frac{0.7^{(1-D)}}{MPE}$$

where MPE is expressed in J/cm$^2$.

(c) If $C_P$>1.0, then set $C_P$ at 1.0.

Thus, methods based on the above may include the system determining, concurrently or sequentially with the tracking, the laser power to deliver to stromal pigment by at least retrieving a set of laser criteria for delivery of an exposure less than 100 times of a maximum permissible exposure that will cause elimination of at least a portion of the stromal pigment. The elimination of the stromal pigment is preferably performed by initiation of macrophagic digestion of the stromal pigment. However, in some implementations, the elimination may be caused by ablation of the stromal pigment. Typically, ablation is caused by higher laser powers than those used to initiate macrophagic digestion.

Laser criteria may include any settings for the laser system such as energy per pulse, spot size, pulse duration, pulse width, repetition rate, beam profile, beam angle, beam position, etc. accordingly, it is contemplated that there may be multiple sets of such laser criteria that satisfy the restriction on the exposure described above. While the above multiple is one example, it is further contemplated that the exposure may be, for example, less than 50 times the MPE, less than 75 times the MPE, etc.

In some implementations, the difference given above may be due to the divergence angle of the beam (i.e., a defocused beam causes a lower power density at the fundus). Various implementations may include generation of a Gaussian beam that may be converging anterior (in front of) to the iris with at least a portion diverging posterior (behind) the iris. The focal plane (i.e., the location of the beam waist) may therefore be anywhere in this range, such as being within the iris itself, but optionally further in front of the iris. When the present disclosure refers to focusing laser power at the stromal pigment, this means that the laser power may be focused at a specific location, which may include, the anterior or posterior surface of the iris, or at a particular cell layer in the iris or stromal pigment layer therein.

The divergence of the beam and the size and location of the beam waist set the spot size at the target. For example, if the beam waist is at the target, the spot size is the beam waist. However, if the beam waist is in front or behind the target, the spot size will be larger based on the convergence or divergence of the beam. Because a spot size does not have sharp edges, the measurement must be defined by a specific measurement convention. Exemplary conventions comprise FWHM, 1/e, 1/e$^2$, Dσ46, 10/90 or 20/80 knife-edge, and D86. Unless otherwise indicated herein, spot size shall refer to spot width, as defined by the 1/e$^2$ convention. Some methods may include determining a spot size for laser light to be delivered to a stromal pigment of an iris of the eye of the patient. The determination may include retrieving a set of laser criteria that result in delivery of laser light having a spot size of 4-70 microns, inclusive, to the stromal pigment. From the available set of set of laser criteria, a particular laser criterion may be selected to control the laser system to generate a laser having a desired spot size. The laser system may be set to deliver the laser light at the spot size and then to deliver the laser light. In some embodiments, the system may determine that spot size may be between 4-50, 10-60, 20-30, 25-30, 20-60, or 30-60 microns. Such spot sizes may be created utilizing at least one positive lens. To deliver an efficacious fluence at the iris plane, but comply with the MPE at the fundus, the forming of such a high divergence angle will create a short depth of focus ("DOF"), defined herein as the focal range within which 90% to 100% of peak fluence is achieved). The DOF will depend not only on the spot size and associated divergence angle, but also the wavelength of the beam. In general, the longer the wavelength, the longer the DOF, ceteris paribus. Thus, the present disclosure contemplates that the spot size, in combination with the laser power, may be selected to be sufficient to cause a concurrent temperature change (and/or possible acoustic effect) in the iris, thereby causing initiation of macrophagic digestion of the stromal pigment while being safe for the patient. In some implementations, the spot size of the laser system may be set (and largely constant) with the laser power being adjusted as described herein (to effect treatment, but still have the exposure at the fundus be below the MPE).

While the above is provided as one enabling example suitable for determination of beam waist/spot size, such should not be considered limiting as the particulars of the calculation may change depending on an individual treatment plan.

In order to achieve the MRE without exceeding the MPE, a relatively high beam divergence angle may be used. As a result, the radius of the beam at its focal plane ($w_0$) may be relatively small as compared to the radius of the beam waist at the fundus plane ($w(z)$).

Equation (4) gives the ratio (S) of $w(z)^2$ to $w_0^2$:

$$S = \frac{R(\lambda) \cdot H(J/cm^2)}{0.02}$$

where

The 0.02 denominator is the base MPE of 20 mJ/cm² for $\mu$=700 nm, converted to J/cm²;

and $R(\lambda)$ is the Thermal Hazard Weighting Function for the $\lambda$ from Appendix 1.

Using the laser parameters from the Exemplary Embodiment, $R(\mu)$=2.10. Equation (4) thus gives the following S ranges:

| MRE | MRE Range (mJ/cm²) | S Range |
|---|---|---|
| MRE I | 250-400 | 25.25-42.00 |
| MRE II | 550-650 | 55.75-68.25 |
| MRE III | 750-850 | 78.75-89.25 |

To avoid having to change $w_0$ for each patient/treatment, a preferred embodiment sets $w_0$ at the highest anticipated MRE so that the $w_0$ will meet the MPE for all MREs. In the example above, the highest anticipated MRE is 0.850 J/cm². This gives us an S of 89.25, meaning that in order to prevent the highest MRE from exceeding the MPE, $w(z)^2$ must be at least 89.25 times $w_0^2$.

To find $w_0$ from S, we can use the following Equation (5):

$$w_o = \sqrt{\frac{\lambda \cdot z}{\pi \cdot n \cdot \sqrt{S-1}}}$$

where $\lambda$=0.000532 mm (converted from 532 nm);

z is the distance in mm from $w_0$ to $w(z)$; and n is the refractive index of the medium through which the beam will travel.

Using 20 mm as the average z from the iris plane to the fundus plane and 1.336 as the n of the aqueous and vitreous fluids of the eye, Equation (5) gives $w_0$=0.0164 mm. The following Equation (6) may be used to find $w(z)$:

$$w(z) = \sqrt{S \cdot w_0^2}$$

Equation (6) gives $w(z)$=0.15519155 mm.

Recall that $w_0$ and $w(z)$ are the radii of the beam at its waist and at the fundus. Therefore, the diameter (as $1/e^2$) of the beam at its waist ($d_0$) is 0.0328 mm, and the diameter (as $1/e^2$) of the beam at the fundus ($d(z)$) is 0.31038 mm.

The DOF of the beam is the total distance (+/−z) from its beam waist. The distance z is given by the following Equation (7):

$$z = \frac{w_0^2 \cdot \pi \cdot n \cdot \sqrt{S-1}}{\lambda}$$

where

S=1/[desired percentage of waist fluence]

$\lambda$=0.000532 mm

The DOF may be defined as that portion of the beam axis where the fluence of the beam is at least 90% of the fluence at the beam waist, i.e., where S=1/0.9. Using this and the other laser parameters from the disclosed example, Equation (7) gives z=0.707312185 mm, and DOF=1.41462437 mm.

This relatively short DOF demands reasonably high-resolution range-finding to identify the location of the initial focal plane and place the beam waist at the desired location in relation to the initial focal plane, as well as reasonably high resolution auto-focusing to maintain the desired location of the beam waist relative to the focal plane. These high-resolution systems are discussed herein. In one implementation, the beam waist may be located within the stromal pigment layer or slightly anterior to the anterior iris surface.

Figure 3:
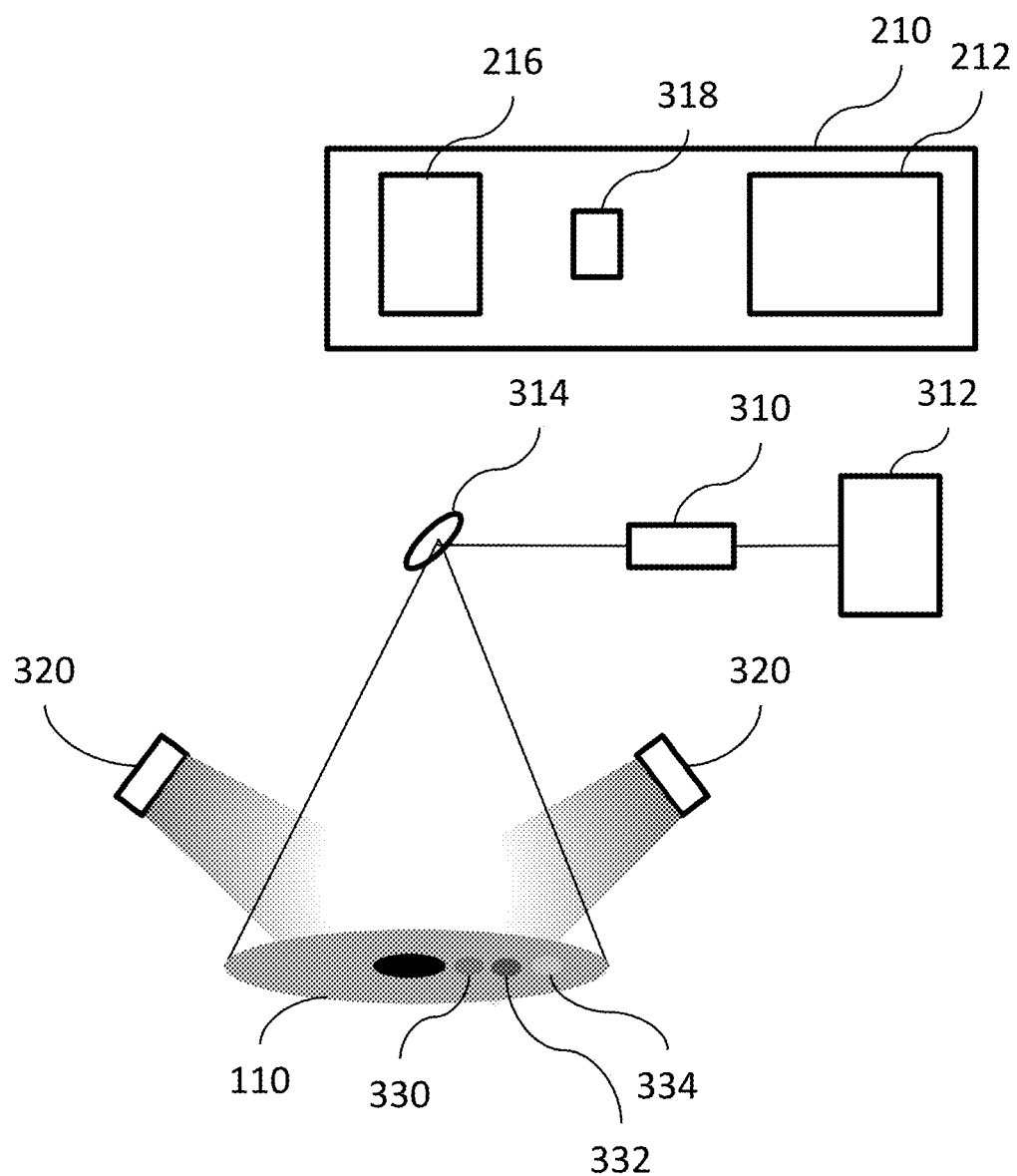
FIG. 3 shows a simplified diagram of a laser system and image sensor for use in mapping the iris in accordance with one or more embodiments.

FIG. 3 shows a simplified diagram of a laser system 210 and image sensor 310 for use in mapping the iris in accordance with one or more embodiments. Determination of the proper laser power may depend on variations in the absorption of the delivered laser power due to inhomogeneities in regions 330, 332, 334 of the stromal pigment layer. Such variations may be caused by, for example, varying density of the stromal pigment, varying sizes of stromal pigment cells, types and compositions of the stromal pigment, etc. As such, regions of the iris where the stromal pigment has a higher absorption coefficient reach a higher temperature (or a target temperature faster) for a given laser power. These differences, if not accounted for, may result in uneven color alteration or possibly even damage to the eye. To address this problem, some implementations of the disclosed methods may include imaging the iris with an image sensor operatively connected to a computer 312 prior to the procedure to generate images of the iris. Examples of image sensors may include a CCD, COMS, or camera used in conjunction with an illumination source 320, wherein the wavelength range of the sensor includes the wavelength of the illumination source. Exemplary wavelengths include near and mid-infrared, visible light, or the specific wavelength of the treatment laser beam. An embodiment might also include software programs capable of creating a digital color model from the captured images and mapping or otherwise analyzing the stromal pigment coefficients for the treatment wavelength based on the model. Exemplary digital color models include RGB (which stands for red-green-blue), HSI (for hue-saturation-intensity), HSL (for hue-saturation-lightness), HSV (for hue-saturation-value), CMY (for cyan-magenta-yellow), and YIQ (luminance-inphase-quadrature).

To facilitate integration of the image sensor with existing laser system, the image sensor may incorporate a dichroic optic 314 (e.g., a dichroic lens, mirror, or prism) to divert incoming light reflected from the iris the reflective or refractive side of the optic and directing it to the image sensor, while allowing outgoing laser light to pass through the optic to the iris surface for treatment. Such implementations have the advantage that the light may be collected on the same optical axis as the laser system. This has the advantage of both simplifying and making more accurate the generation of the mapping relative to the geometry of laser system because it avoids the need to account for an off-axis image sensor.

Based on the images, a mapping of the iris may be generated by the system and may contain regions corresponding to varying absorption coefficients of a treatment wavelength in the stromal pigment of the iris. As shown in FIG. 3, regions 330, 332, 334 are depicted to indicate different absorption coefficients. The mapping may be, for example, 2D (or 3D) data having pixels or voxels of the imaged iris with each pixel or voxel having a corresponding calculated absorption coefficient. The mapping need not be stored at the pixel/voxel level but may also be in terms of larger regions (e.g., combining pixels/voxels that may have similar absorption coefficients (e.g., utilizing a watershed algorithm). In other embodiments, regions may be specified at the subpixel/voxel level by performing 2D (or 3D) interpolation of neighboring pixels/voxels to provide a continuous function of absorption across a pixel/voxel.

As mentioned above, generating the mapping may include calculating absorption coefficients at the wavelength of the laser light in various regions of the iris. The present disclosure contemplates numerous implementations for calculating the absorption coefficients. For example, the image sensor (or data obtained with such) may measure the absorption or reflectivity of predetermined wavelengths within the image of the iris to determine the absorption coefficients. The fluence needed to increase the temperature in the target stromal pigment and thereby initiate the biological reaction necessary to remove the target pigment is a direct function of the absorption of the energy of the laser light in the pigment. Thus, by determining the absorption coefficient of the stromal pigment in a particular region for the given wavelength, the system can accurately determine and deliver the laser power needed for pigment removal.

The system may include various apparatuses for determining the absorption coefficients, such as those used with hyperspectral imaging ("HSI"): scanning electron microscopy ("SEM") images with color modeling (e.g., RBG, HSI, HSL, HSV, CMY, and YIQ) using filters appropriate for the laser wavelength.

To map the pigment density, various kinds of light may be used by the system, for example, infrared or visible. In some implementations, the saturation channel of an iris image may provide a very good estimate of stromal pigment density. In other embodiments, the system may use blue or green channels of the image. In yet other embodiments, the system may use monochrome infrared for an approximation of stromal pigment.

Specifically, in some embodiments, the reflectivity of the image is based on an inverse of the saturation in the image. The system may determine reflectivity, saturation, etc., on a pixel by pixel basis or over wider regions of the image. For example, based on analyzing intensities of received light at the imaging sensor, the system may break up the iris into regions of similar intensities (e.g., within 1%, 5%, 10%, etc.). The system may determine the average reflectivity and/or saturation of these regions for determining the absorption coefficient for all points of delivery of light in that region.

Several optional features are disclosed to aid in obtaining more accurate measurements for determining absorption coefficients. First, the illumination source may have the same (or approximately the same—e.g., within 5% or 10%) of the wavelength delivered by the laser system. For example, if the planned treatment incorporates a 1064 nm laser, then the illumination source may provide infrared light covering that wavelength. Similarly, if the laser wavelength is to be 532 nm (green), then the illumination source may provide green light. Also, in certain implementations, this imaging may further include filtering the reflected light received from the stromal pigment at the image sensor through a bandpass filter configured to pass a wavelength corresponding to the laser light and/or illumination source. In yet other implementations, the system may include a similar bandpass filter at the illumination source, for example, if such sources are more broad-spectrum than desired.

The laser system may also include a power modulator 318 to vary the laser power based on the determined mapping. Exemplary optical power modulators may include: acousto-optic modulators; electro-optic intensity modulators; electro-absorption modulators; semiconductor optical amplifiers; and liquid crystal modulators. A structural embodiment of an exemplary acousto-optic modulator may include a transducer that generates a sound wave that partially diffracts the laser beam. A structural embodiment of an exemplary electro-optic intensity modulator may include a Pockels cell between two polarizers. The Pockels cell modulates the phase of the beam, and the polarizers transform the phase modulation into an intensity modulation. The Pockels cell may have a single crystal or two or more crystals to reduce its power requirements. The polarizers may be replaced by an interferometer, as in the case of a Mach-Zehnder modulator. A structural embodiment of an exemplary electroabsorption modulator may include one or more semiconductor devices operating on the Franz-Keldysh effect. Such modulators may operate on light in a waveguide and may be coupled to optical fibers or placed on a chip together with other components, such as a laser diode to form a telecom transmitter. An exemplary semiconductor optical amplifier used as an intensity modulator includes a semiconductor optical amplifier, with or without drive current. Without drive current, the amplifier provides some degree of attenuation as negative gain. When supplied with pump current, attenuation is achieved as positive gain. An exemplary liquid crystal modulator applies a voltage to a liquid crystal material to modulate light polarization and obtain intensity modulation by adding a polarizer.

Figure 4:
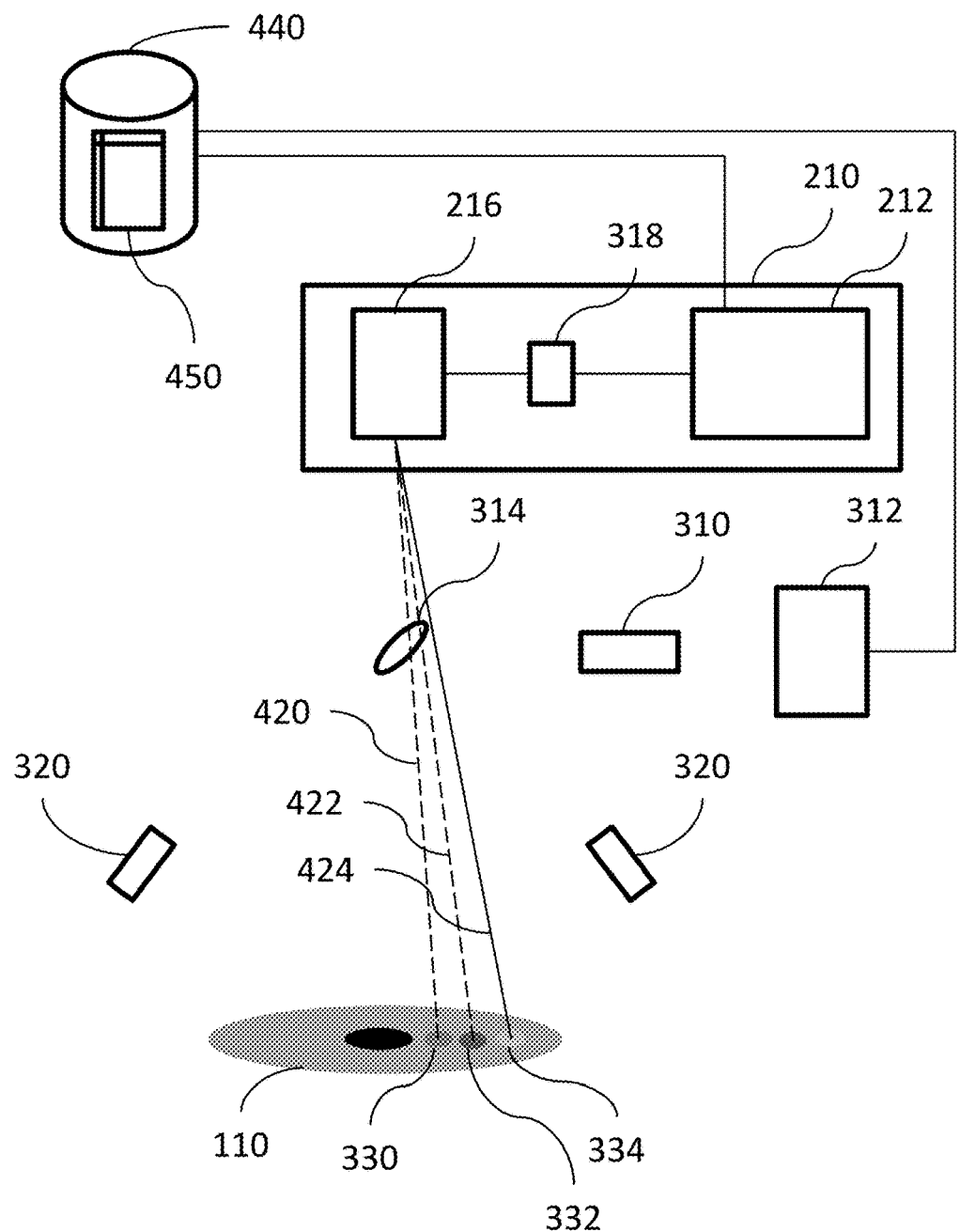
FIG. 4 shows the system of FIG. 3 delivering variable laser power to regions of the iris in accordance with one or more embodiments.

FIG. 4 shows the system of FIG. 3 delivering variable laser power to regions of the iris in accordance with one or more embodiments. With the mapping derived as noted herein, the power modulator may control delivery of laser power that accounts for the regions having different absorption coefficients. As the laser light scans the target areas of the iris, when a region is reached that is a different absorption coefficient, the system may control the power modulator to adjust the laser power accordingly. For example, the system may set the laser power based on the mapping such that regions of higher absorption coefficients receive a lower laser power than regions of lower absorption coefficients. This is depicted by exemplary laser beams 420, 422, and 424 which correspond to the regions 330, 332, and 334. The system may modulate the laser power delivered with such beams utilizing the power modulator described above. For pulsed operations, this may include delivering a set laser energy per pulse to the regions based on the absorption coefficients. Again, the set laser energy may be determined to be a multiple of the MPE, as described elsewhere herein.

As mentioned above, while the system may calculate the absorption coefficient on a pixel-by-pixel basis, it may be beneficial in some implementations to assign pixels in the iris image to a particular "region" that will receive the same laser power. Such implementations may be performed by the system as a binning operation where pixels with calculated absorption coefficients in a first range get assigned to a first region, and a second range get assigned to a second region, etc. As shown in FIG. 4, the computer 312 associated with the imaging system may be in communication with computer or database 440 that receives as input the image of the iris or instead some or all values of pixels from the image. In some implementations, computer 440 may then access lookup table 450 to determine the set of laser criteria to be utilized by the laser system for delivering laser power to that region. A simplified example of a lookup table is below. The exemplary laser powers are listed as a multiple of the maximum permissible exposure, as explained herein. These powers (based on a 1,064 nm laser wavelength) are examples that may be appropriate for pigmentation that gives a dark brown (having corresponding MRE I, as described above), medium brown (e.g., MRE II), or tan (e.g., MRE III) coloration, respectively.

| Region | Abs. coeff. (cm$^{-1}$) | Power (xMPE) |
|---|---|---|
| 1 | 2070-2270 | 34 |
| 2 | 2270-2470 | 63 |
| 3 | 2470-2670 | 84 |

As used herein, the term "region" refers to any area or areas of the iris of similar pigmentation, and such area or areas need not be continuous. For example, in the context above when discussing regions of similar pigment, a particular iris may have an area of reduced pigment. There could be another area having essentially the same pigmentation but in another location in the iris that is not touching the first area. In accordance with the method disclosed above, the positions in the images of the iris (e.g., pixels or their equivalent locations on the scanning pattern described herein) could all fall into the same "region" if their respective absorption coefficients require such (e.g., as illustrated by the exemplary table above).

The system may also be configured for blanking the beam wherever there is little or no stromal pigment. Beam blanking can be accomplished in a number of ways, including deactivating the laser, deflecting the beam into a beam dump using an optic such as a prism or mirror, or reducing the radiative power to a subclinical level using the energy modulator disclosed elsewhere in this Application. Deactivating the laser may, in some cases not be utilized due to time delays and other potential complications upon reactivation.

In one embodiment, anterior iris regions are selected or deselected for blanking automatically by illuminating the anterior iris, using a CCD or other camera to capture an image of the anterior iris surface, transmitting the image to a computer with an image analysis software program (such as Celleste Image Analysis Software, Thermo Fisher Scientific Inc., Waltham, MA, USA), identifying the pigmented regions, generating a lookup table comprising the coordinate ranges of the pigmented regions, and coordinating with the beam guidance software and energy disruption or modulation software to blank the treatment beam everywhere outside of the pigmented regions.

In an alternate embodiment, anterior iris regions may be selected or deselected for blanking manually by automatically by the system illuminating the anterior iris, capturing a still or moving image a CCD or other camera, displaying the image on the user interface touch screen, inviting the operator to outline the regions he or she wishes to blank or irradiate, and inviting to operator to elect (e.g., via icons on a GUI displayed on the same screen) whether the outlined areas are to be treated or blanked. The display computer and software may display the operator-drawn outlines on the display, generate a lookup table comprising the coordinate ranges of the outlines, and coordinate with the beam guidance software and energy disruption or modulation software to blank the treatment beam everywhere inside or outside (as selected) of the outlined regions.

One of the advantages of these selective beam blanking implementations is that without it, re-treating the anterior iris surface after the pigment has been removed might result in the elimination of additional stromal pigment from within the iris stroma, which, as discussed herein, will likely increase color saturation, which might be contrary to the patient's preferences.

The color alteration procedure described herein may be divided into multiple stages of treatment to remove different amounts or types of stromal pigment at different times. Stromal pigment, as previously discussed, may have varying physical properties that affect its responses to delivered laser power. Some stromal pigment may require a higher laser power to raise its temperature such that it may be removed via macrophagic digestion. Thus, after a first treatment at a lower power, there may be some stromal pigment that needs to be removed and require a higher laser power to do so. In this way, some methods of treatment may include determining, as part of the color alteration procedure, stages of delivery of laser power to the iris such that successive stages cause removal of less pigment but are delivered at a higher laser power. Thus, a given treatment session may include setting the laser system to the required laser power further based on a current stage of delivery and delivering the laser power based on the setting. A treatment session may include any number of stages of delivery, though typically a treatment session includes only one stage of delivery as days or weeks may be needed for removal of the denatured stromal pigment.

In some implementations, the system may deliver laser power over a number of steps to allow finer control of pigment denaturation. This may be a safety feature of the system to ensure that the lowest power is applied to the cells with the highest absorption coefficient to avoid ablation, that the highest power is applied to the cells with the lowest absorption coefficient to achieve efficacy, and that the intermediate powers are applied to the cells with the intermediate absorption coefficients to avoid ablation and achieve efficacy.

For example, as illustrated below, in one exemplary embodiment based on the above-described multiples of MPE, an arbitrary number of sub-ranges can be established and laser power may be delivered within those subregions. In the table below, the "Total Range" is reproduced from above. For each of the eye colors, an example five sub-ranges are shown, but the system may deliver any number of sub-ranges (e.g., 2, 3, 7, 10, etc.) of laser power. Another optional feature reflected in the below example is that the sub-ranges are chosen to overlap with the adjacent sub-range. In the example below, the overlap is 20%, however, this can vary in other implementations for example, 5%, 10%, 30%, etc.

| Color | Total Range (×MPE) | Subrange I (×MPE) | Subrange II (×MPE) | Subrange III (×MPE) | Subrange IV (×MPE) | Subrange V (×MPE) |
|---|---|---|---|---|---|---|
| Dark Brown | 25.4-42.6 | 25.4-26.6 | 29.4-30.6 | 33.4-34.6 | 37.4-38.6 | 38.4-42.6 |
| Medium Brown | 57.5-71 | 57.5-61 | 60-63.5 | 62.5-66 | 65-68.5 | 67-71 |
| Tan | 78.5-92 | 78.5-82 | 81-83.5 | 62.5-87 | 86-90.5 | 88-92 |

Thus, in one implementation, the system may be configured to provide multistage delivery where there are at least three stages. In this example (for dark brown eyes), a first stage of the three stages may deliver approximately 26 times MPE to the stromal pigment, a second stage may deliver approximately 30 times the MPE to the stromal pigment, and a third stage may deliver approximately 34 times the MPE to the stromal pigment.

Figure 5:
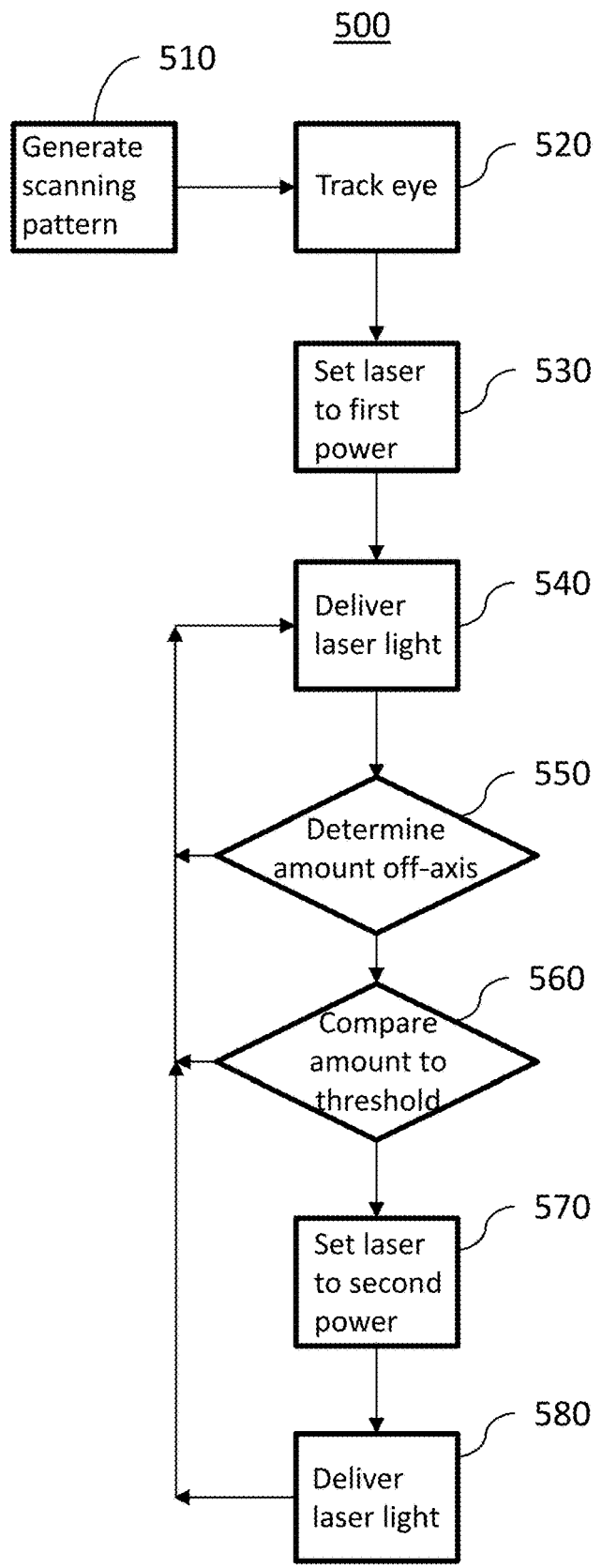
FIG. 5 shows a process for monitoring the alignment of the eye during the delivery of laser power in accordance with one or more embodiments.

FIG. 5 illustrates a process 500 for monitoring the alignment of the eye during the delivery of laser power as described herein. As previously mentioned, and as will be explained in further detail below (see FIG. 6), at 510, the process may include generating a scanning pattern and deliver the laser power according to the scanning pattern. In some implementations consistent with the color alteration procedures disclosed herein, the laser power may be delivered to at least 50% of an anterior surface of iris of the patient—e.g., to remove some pigment from most if not all of the iris to provide a uniform color change.

During the procedure, at 520, the process may include tracking the eye. For example, the system may utilize an optical tracking system to track an axial alignment of the eye of the patient. As used herein, "axial alignment" refers to having the iris (or equivalently the center of the pupil to provide a single point of reference) in an acceptable location on the X-Y plane in which the laser will be scanned around to deliver laser power to the iris. Examples of what is considered acceptable are provided below for various implementations.

At 530, the laser system may be set to deliver laser radiation at a first laser power. For example, the system may deliver the first laser power to a location in the eye, with the first laser power sufficient to cause elimination of at least a portion of stromal pigment in an iris. Then, at 540, the laser system may deliver the laser light. For example, the system may deliver the laser light to the eye, according to the scanning pattern, at the first laser power.

To maintain proper alignment between the patient and the laser system, the process may further include, at 550, determining an amount that the eye is off axis. This determination may, for example, be made by the system based on the axial alignment. In implementations where the axial alignment is determined at the iris plane, the amount off axis may be considered as the distance between the optical axis of the laser system and the center of the pupil. In some implementations, this may involve the system performing imaging (e.g., infrared imaging or other imaging techniques previously discussed) of the iris during the procedure. However, in some implementations, axial alignment may be determined by the system based on images received of different parts of the eye (e.g., the limbus) or even based on information not relating to the eye (e.g., the position or tilt of the patient's nose or forehead). In such cases, a geometric conversion may be performed by the system to convert the received axial alignment to the amount off axis. For example, a measured rotation of the patient's head and a known distance from the axis of rotation to the iris plane may be utilized by the system to convert the measured rotation to the X-Y amount off-axis. If the eye is not off axis, delivery may continue as in 540 according to the scanning pattern and laser criteria, at the first laser power.

If it is determined that the eye is off axis, then, at 560, the system may compare the amount off axis to a first threshold amount. Ranges for various first threshold amounts may include, for example, 300-400 μm, inclusive; 400-500 μm, inclusive; 500-750 μm, inclusive; 750-1000 μm, inclusive; and 1000-2000 μm, inclusive. Examples of first threshold amounts may include, for example, 100 μm, 200 μm, 300 μm, 500 μm, 750 μm, 1000 μm, etc. If the amount off axis is below the first threshold amount, then delivery may continue as in 540. Otherwise, in some implementations, at 570, the laser system may be set to a second laser power. For example, the system may make this setting based on the system determining that the amount equals or exceeds the first threshold amount. As this describes likely an undesirable condition, some implementations may have the second laser power be less than the first laser power (or even a nominal power). At 580, the laser system may deliver laser light to the eye at the second laser power. For example, the delivery may be according to the scanning pattern. The delivery may continue (essentially returning to step 540 but at the lower power while the eye remains off-axis). Alternatively, the delivery of laser power may stop entirely.

Figure 6:
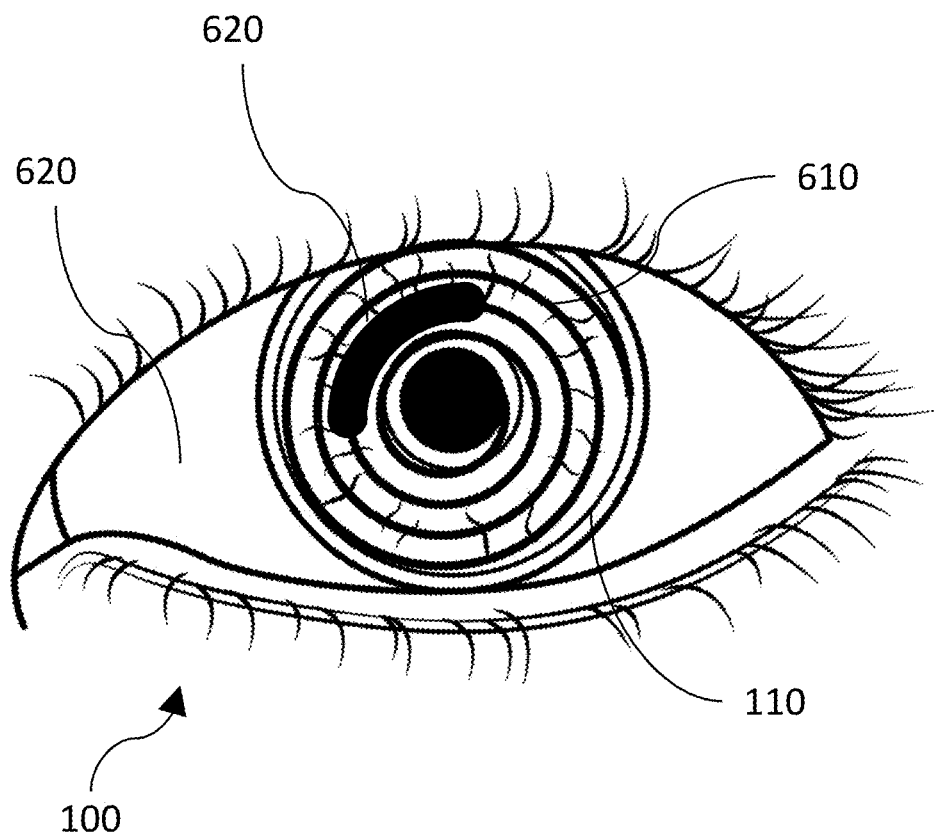
FIG. 6 shows a scanning pattern and partial treatment area superimposed on the iris in accordance with one or more embodiments.

FIG. 6 illustrates a scanning pattern 610 and partial treatment area 620 superimposed on the iris 110. As described herein, the delivery of laser radiation may be according to a scanning pattern where a substantial amount of the pigment in the iris is treated to provide the desired and uniform color change. In some implementations, the generation of the scanning pattern may include imaging the iris with an image sensor (e.g., an infrared camera, visible camera, etc.) prior to the procedure. This scanning may generate an image of the iris, which may be stored as part of the patient's medical record or treatment plan. As part of generating the scanning pattern, some implementations may include performing boundary detection on the image to determine a pupil boundary and a limbus boundary. The pupil boundary may be taken to approximate the inner boundary of the iris, and the limbus may be taken to approximate the outer boundary of the iris. Boundary detection algorithms that may be used on the image may include, for example, Canny edge detection, phase congruency (or phase coherence) methods, etc.

With a determined boundary(s) of the iris, some methods may include generating the scanning pattern to cover at least 50% of the anterior surface of the iris based on a laser spot size. In other implementations, the area of the anterior surface of the iris covered by the scanning pattern with a given laser spot size may be, inclusive, 50%-60%, 60%-70%, 70%-80%, 80%-90%, or 90%-100%. As may be seen in FIG. 6, the scanning pattern sets the path of the laser beam, but the spot size at the iris in combination with the scanning pattern determines the area that is treated. A portion of a treatment area is depicted in FIG. 6 as the thick black band representing the partial treatment area 620 running along the scanning pattern. It is noted that the scanning pattern and spot size (i.e., thickness of the band) are exaggerated for illustrative purposes. As mentioned above, because many patients desire a uniform eye color change, this necessitates performing the disclosed laser operations on a large fraction of the iris area. In some implementations, this may include delivering laser power to at least 35%, at least 50%, at least 60%, at least 75%, at least 90%, or substantially 100% of the anterior surface of the iris. In an embodiment, it is contemplated that there may be locations in the iris where there is little to no pigment to be treated and thus such locations may be skipped or blanked. In this way, even if there is a general intent to treat for example 100% of the iris, there may be small areas that are not treated. As such, substantially 100% of the iris may be covered by these scanning patterns.

The exact scanning pattern generated may be a function of the laser spot size in that the selection of the distance between adjacent laser spots may be chosen to provide a desired (or acceptable) degree of overlap and/or separation. For example, for adjacent laser spots that are only touching but not overlapping, there will be points in between that will receive less laser energy during the sweep of the laser through the scanning pattern. Accordingly, in some implementations, there may be some overlap between adjacent laser spots, and this will affect the specific scanning pattern coordinates utilized by the laser system.

As the boundaries of the iris tend to be very good approximations of circles. For example, the iris width (i.e., the transverse horizontal diameter) is generally about 2% greater than the iris height (i.e., sagittal vertical diameter). Accordingly, some implementations may include generating the scanning pattern to be a spiral pattern extending from approximately the pupil boundary to approximately the limbus boundary. While the spiral pattern (which may spiral in or out as selected) may be a natural choice, in other implementations, a square or rectangular back-and-forth raster may be implemented where the scanning pattern consists of generally linear segments with multiple turnarounds to sweep out the area to be treated. Where the scan pattern extends beyond the desired treatment boundary, the beam may be skipped or blanked.

Some implementations may include the system delivering one or more scans per treatment session. In such implementations, one "scan" may be defined as a single application of laser spots to the predetermined X-Y treatment area on the iris, using the predetermined scan pattern and the predetermined spot overlap and/or separation. Thus, for example, a treatment session may include 1-250 scans, inclusive, with other implementations having 5-20 or 10-15 scans, inclusive, per treatment session.

Provided here are further details of some implementations of the methods disclosed above for tracking the alignment of the eye. In some implementations, the second laser power (e.g., after an off-axis determination) may be insufficient to cause elimination of at least a portion of the stromal pigment. In this way, rather than turning the laser off entirely, the second laser power may be used where the laser is not harmful to the iris and does not have an effect on the treatment. Once alignment is reestablished, then first laser power may also be reestablished, and the treatment may continue. In other implementations, some correction may be provided by the system adjusting a delivery position of the laser system to compensate or at least partially compensate for the amount off axis. This may include, for example, shifting or tilting the laser system (or one or more components thereof such as a lens or mirror) or shifting or tilting the patient in order to shift or tilt the eye. Depending on the implementation, there may or may not be a change of angle or tilt. The system may, in some implementations, perform a shift or tilt to compensate for the shift or tilt of the iris. The shift or tilt of the iris may be detected by the imaging system, whereby images of all or some portion of the eye may be captured at predetermined intervals by a CCD, camera, or other image capture device and transmitted to a software program residing on a computer. The software program may compare each image to a previous image. If the software detects a change in the position of the eye indicating a shift or tilt in the position of the iris, the software may calculate the amount of the shift or tilt and instruct either (a) the beam guidance system to shift or tilt the position of the scan pattern to compensate for the iris shift or (b) the patient support system to shift or tilt the position of all or some portion of the patient to compensate for the iris shift.

In implementations where a gaze fixation target is used, any such shift or tilt, within or exceeding the predetermined threshold, may likely be temporary and brief as the patient's gaze will likely return quickly to the target. Therefore, passive tracking as disclosed herein may be especially appropriate in such implementations.

In some implementations, some allowance may be made for small misalignments below another threshold. For example, certain implementations may include comparing the amount (of misalignment) to a second threshold amount (e.g., 250 µm), which may be less than the first threshold (e.g., 500 µm). In this example, the treatment would continue without any adjustments to the delivery angle/position if the misalignment is less than 250 µm, would move the beam optics and/or patient to compensate for misalignments between 250-500 µm, and would reduce laser power or stop if over 500 µm. Ranges for various second threshold amounts may include, for example, 50-100 µm, inclusive; 100-200 µm, inclusive; 200-300 µm, inclusive; 300-400 µm, inclusive; 400-500 µm, inclusive; 500-750 µm, inclusive; and 750-1000 µm, inclusive. In varying embodiments, the second threshold amount may be approximately 10 µm, 50

μm, 75 μm, 100 μm, 150 μm, 200 μm, 250 μm, 300 μm, 350 μm, 400 μm, 450 μm, 500 μm, 550 μm, etc. Determination of the threshold amounts may take into account the minimum amount of shift or tilt that could occur before a portion of the scan pattern would enter the pupil of the iris and pose a safety risk to the fundus of the eye. As small misalignments below the second threshold may not require a change in laser power, the laser system may be controlled to move the laser light in a horizontal plane while keeping the laser light substantially perpendicular to the iris and while maintaining delivery of the laser light at the first laser power. This controlling may be done by the system operating the galvos of the laser system to direct the light to an off-axis X-Y location in the iris.

Figure 7:
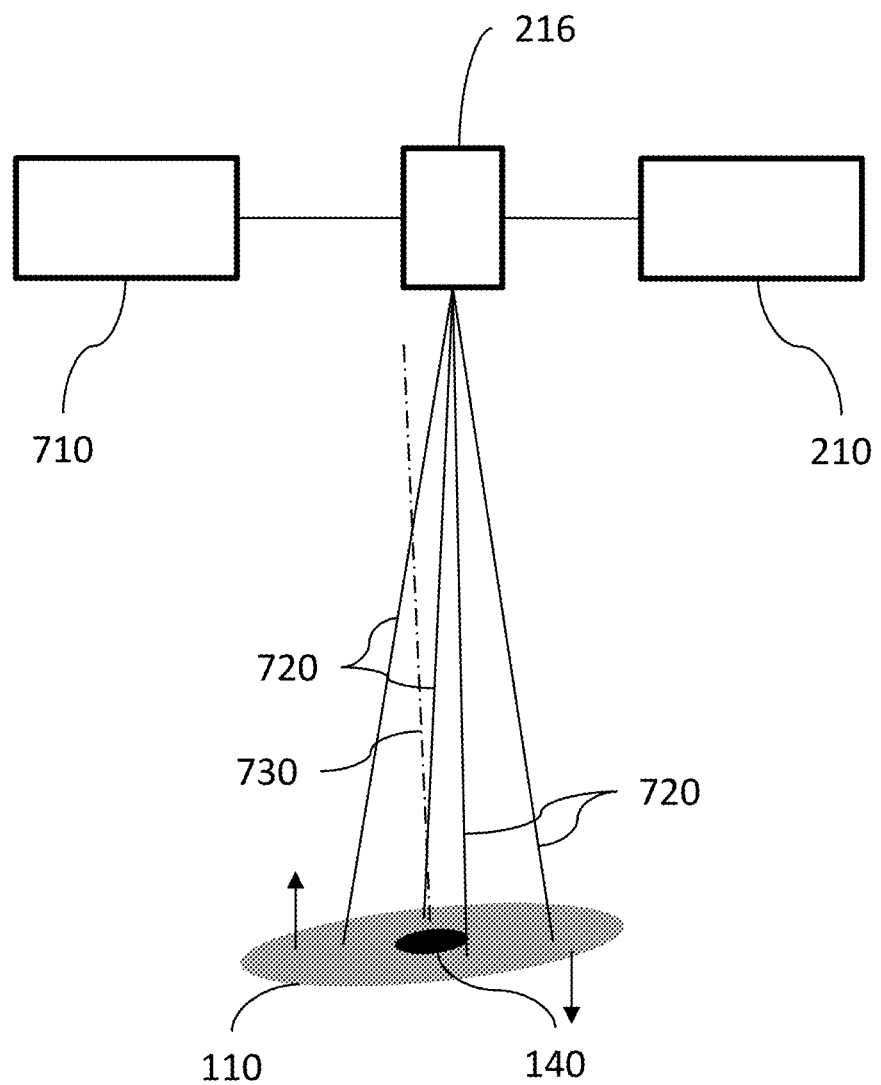
FIG. 7 shows a pupil that is tilted with respect to a laser beam and a rangefinder used to determine the degree of tilt of the iris in accordance with one or more embodiments.

Tilt Detection (FIG. 7)

FIG. 7 illustrates an iris that is tilted with respect to a laser beam and a rangefinder used to determine the degree of tilt. As has been described elsewhere herein, the treatment delivered to the iris is generally along a horizontal (X-Y) plane, and a key consideration in the delivery of the laser power is to have the laser focused at the proper location (i.e., not above or below where it is supposed to be focused). Accordingly, if the iris were tilted, and such tilt were not accounted for, then the focus of the laser beam would be anterior or posterior to the expected focal position on the X-Y plane. Accordingly, this may alter the delivered power or energy density and may thus result in an inefficacious treatment or even injury to the eye. Disclosed herein are methods that may prevent this from occurring based on determining the tilt and compensating for or correcting it. In some implementations, rangefinder 710 may be utilized to determine the distance from a reference point (e.g., a mirror, a light source, etc.) to the iris. As depicted in FIG. 7, a simplified example of a tilted iris is shown, specifically with the iris tilted about the Y-axis (in/out of the page). The angle between the normal 730 to the iris plane and the axis of the laser system (taken to be the vertical or Z-axis) is the tilt angle. Because the iris may tilt around both the X axis and Y axis, the tilt may be expressed as a vector quantity with components in both directions.

The method may also include determining, with the rangefinder that is part of an optical tracking system, an amount of tilt of an iris based on the optical tracking system interpreting optical data received at the optical tracking system from the eye. The distance measured by the rangefinder to different points on the iris (e.g., along one or more paths 720) may be used to determine the tilt of the iris by establishing three or more points on the iris to thus define the iris plane. The example in FIG. 7 depicts an implementation where four distances (e.g., with Z-tracking as disclosed herein) are determined, which may correspond to four different quadrants of the iris to capture tilt around both the X axis and Y axis. Knowing the iris plane, the system may determine its normal and thus the amount of tilt (tilt angle) may be calculated.

Some implementations of the disclosed methods may include utilizing a rangefinder as part of the optical tracking system to provide accurate distances to the target location in the eye. For example, the rangefinder may determine a distance between the iris and a reference component of the optical tracking system. Examples of reference components may include the last optical component in the laser system (e.g., a window or lens closest to the patient), a mirror or galvos, or any other component or location in the laser system with a known location to provide a point of reference for the rangefinding.

Based on the determined distance, the system may control shift the focal point of the laser beam to remain substantially in focus between an anterior surface and posterior surface of the iris, at the stromal pigment targeted for removal, or at any of the disclosed possible focusing planes. Examples of rangefinders may include, for example, triangulation lasers, time of flight detectors, phase shift detectors, ultrasonic detectors, frequency modulation detectors, interferometers, a camera, or a light sensor.

Triangulation may utilize lasers for distance measurements. Structural embodiments of exemplary triangulation methods may include three elements: an imaging device, an illumination source, and either an additional imaging device or an additional illumination source. Illumination source(s) may include image projectors that project light images onto the iris, sclera, or other patient field. Exemplary light images might include circles and lines. In one embodiment, the laser beam may illuminate a point on the surface of the target (e.g., the iris, the sclera, or some other point on the patient's face). Diffuse or specular reflections from the illuminated point may be monitored with a position-sensitive detector, which may be placed a given distance from the laser source such that the laser source, the target point, and the detector form a triangle. Assuming the beam incidence angle to the target is 0°, the position-sensitive detector identifies the incidence angle of the detector to the target, and the distance between the laser source and the detector is known, the distance from the laser source to the target may be determined with the appropriate trigonometric function.

Time-of-flight or pulse measurements may measure the time of flight of a radiation pulse from the measurement device to the target and back again. Exemplary forms of radiation include light (e.g., near-infrared laser) and ultrasound. An exemplary time-of-flight apparatus includes a radiation source, a radiation sensor, and a timer. Time of flight may be measured based upon timed pulses or the phase shift of an amplitude modulated wave. In the case of timed pulses, the speed of the radiation is already known, so the timer measures the turnaround time of each pulse to determine the distance, where distance=(speed of radiation×time of flight)/2.

The phase shift method may utilize an intensity-modulated laser beam. The phase shift of intensity modulation may be related to the time of flight. Compared with interferometric techniques, its accuracy is lower, but it allows unambiguous measurements over larger distances and is more suitable for targets with diffuse reflection. For small distances, ultrasonic time-of-flight methods may be used, and the device may contain an aiming laser for establishing the direction of the ultrasonic sensor, but not for the distance measurement itself.

Frequency modulation methods may include frequency-modulated laser beams, for example with a repetitive linear frequency ramp. The distance to be measured may be translated into a frequency offset, which may be measured via a beat note of the transmitted and received beam.

Interferometers may be implemented for distance measurements with an accuracy which is far better than the wavelength of the light used.

Various systems for rangefinding may provide very accurate measurements, for example, determining distances with the resolution of at least 10-20 μm. Such systems may include, for example, a time-domain optical coherence tomography system or a spectral domain optical coherence tomography system.

Utilizing the disclosed rangefinding, some methods may utilize the same structure to include autofocusing the laser system in response to changes in the determined distance and corresponding shifts in the focal point of the beam. Computer systems in communication with the laser system may automatically autofocus the laser system and measure a distance to the stromal pigment of the iris at periodic intervals (e.g., at approximately 1 kHz, 10 KHz, 100 kHz, etc.).

Exemplary methods for lens focusing include manually or electronically (a) shifting the position of one or more focal lenses (e.g., a lens mounted on a motor stage to shift along the beam access), (b) shifting the position of one or more focal mirrors (e.g., by adding a third mirror to a galvos beam steering system), (c) changing the shape of one or more focal lenses or mirrors, (d) deflecting or refracting a beam by means of an acousto-optical or electro-optical devices, or (e) using electrostatic or electromagnetic lenses or mirrors to shift the focal position of the beam.

Movement of the patient's head and eyes along the z axis can frustrate accurate range-finding and autofocusing. By positioning the patient such that the head is supported and the neck muscles are permitted to release, z head position changes may be minimized.

Topographical variations in the anterior iris surface may also frustrate accurate range-finding and autofocusing. These variations result primarily from three elements: iris tilt, iris folds, and iris crypts. Iris tilt is a naturally occurring phenomenon. As a result, the iris plane will rarely reside perpendicular to the beam axis. The iris plane tilts about both its the horizontal and vertical axes, and can tilt as much as 5°, which results in z variations of up to 700 μm from one edge of the iris to the other (assuming a roughly 11 mm horizontal iris diameter). An iris tilt system may be utilized to significantly reduce or eliminate this iris surface variation.

Iris folds are also a naturally occurring phenomenon. As the iris dilates, it folds like a drape, concentric to and away from the pupil. These folds can create significant z variations in the iris topography. To significantly reduce or eliminate iris folds, some methods may include introduction of a topical miotic solution, such as Pilocarpine ophthalmic solution. In one embodiment, patents may be dosed with 1 drop of 2% Pilocarpine ophthalmic solution 15, 10, and 5 minutes prior to the procedure to achieve high miosis, resistant to the potentially dilative effect of lasing the iris anterior to the iris dilator muscles during the procedure. Each patient may also be given 500 mg of acetaminophen (orally) 30 minutes prior to the procedure as a prophylaxis against headaches from ciliary body tension.

Iris crypts are another common phenomenon. They are created by spaces between the iris stromal fibers. In brown eyes, these crypts are typically filled with pigment and can therefore be ignored for purposes of the initial treatment sessions. Once the stromal pigment has been substantially eliminated outside of the crypts, stromal pigment might remain in the depths of the iris crypts. Pigment spots occur naturally in light eyes, so this remaining crypt pigment should not look unnatural and should barely be noticeable.

If remaining pigment spots bother the patient, the system can remove or reduce the remaining crypt pigment by slightly shifting the beam waist posteriorly into the stroma and rescanning the iris using this shifted waist position. This shifted waist setting may also be an option displayed for selection by the operator on the touch screen interface. The distance of the shift of the beam waist may be equal to about 80% of the beam DOF to ensure delivery of high fluence within the pigmented crypts. If the crypt pigment remains 3-4 weeks after treatment with this posterior waist shift, this waist shift procedure may be repeated, posteriorly shifting the beam waist each time by another 80% of the DOF, until the crypt pigment is eliminated sufficiently eliminated.

In other embodiments, rangefinding may also be used to determine and account for tilts due to the anatomy of the patient's eye. For example, if the patient's optic nerve is not in a typical position relative to the axis through the center of the pupil and lens. To determine the tilt due to such an anatomical condition, the method may include generating a Purkinje image on the cornea (e.g., the first Purkinje image), which may serve as a reference image. Also, as above, the system may determine the boundary of the pupil and thus a center of the pupil. Because the Purkinje image and the pupil are at different depths in the eye, if the iris is tilted the center of the pupil will be offset relative to the Purkinje image. Utilizing the position of the Purkinje image of the cornea and the known boundary/center of the pupil, the tilt may be determined as the angle between the pupil and the Purkinje image. This angle may be added to any other tilt angle determined as described herein to arrive at a total tilt angle, which may then be corrected/compensated for by any of the methods disclosed herein.

Figure 8:
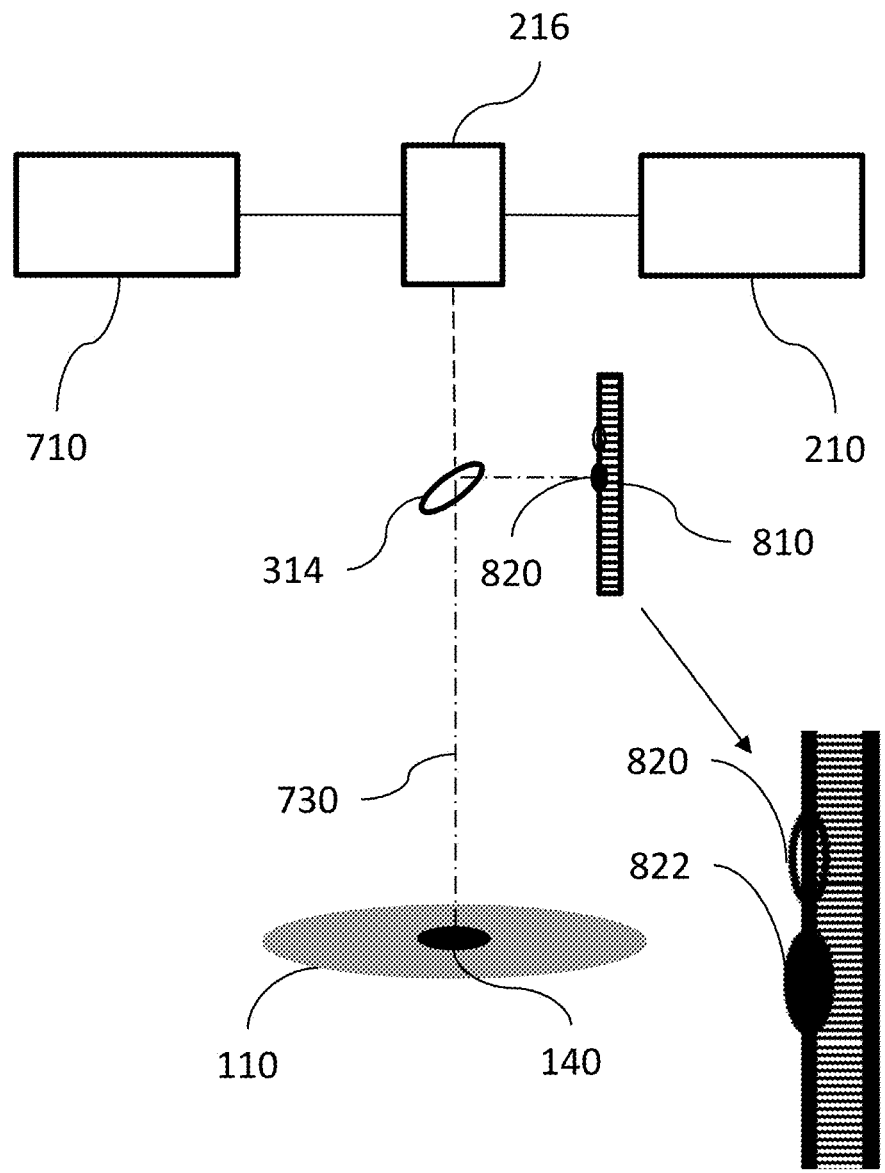
FIG. 8 shows a system utilizing a fixation device to correct or compensate for iris tilt in accordance with one or more embodiments.

FIG. 8 depicts a system utilizing a fixation device to correct or compensate for iris tilt. As described further below, a "fixation device" 810 may be any device upon which the patient may fixate their gaze (e.g., a "fixation target" 820) and thus keep the eye steady during the procedure.

Beginning with the above determination of an iris having some amount of tilt, the system may compare the amount of the tilt angle to a threshold amount. A computer system may then determine, if appropriate, that the amount equals or exceeds the threshold amount. For example, no correction may be needed if the tilt is small. Accordingly, the threshold amount may be, in various embodiments, 10°, 5°, 1°, 1/2°, 1/3°, 1/4°, 1/5°, 1/10°, etc. If the threshold amount is exceeded, then the system may adjust a fixation target characteristic (e.g., an X-Y and/or other position of the fixation target) to cause the patient to shift their gaze, thereby compensating for the amount of tilt. This procedure may be repeated one or more times to ensure that the degree of tilt has been sufficiently reduced or eliminated. With such an adjustment, the laser system may be set to the desired laser power and may be delivered by the laser system as discussed in other embodiments disclosed herein.

The disclosed embodiments of fixation devices and targets may provide numerous ways to keep or restore the position of the eye to that needed for the procedure. In general, the fixation target characteristic may be an appearance and/or a position of the fixation target. This is depicted in FIG. 8 by the fixation target 822 (and the inset showing an enlarged view of the fixation target) being represented as a spot that the patient sees via the mirror 314.

To correct for the tilt determined in the previous example, the fixation target 822 may move downward from a prior position 820 (represented by the open oval) toward the patient. This downward shift in the fixation target causes the normal 730 to rotate clockwise (relative to that shown in FIG. 7) to bring it into line with the axis of the laser beam and thereby correct for the tilt observed in FIG. 7.

In some embodiments, the fixation device may be an LED array (either a 1D arrangement of elements in a lineor 2D pattern such as a picture). The fixation target may be generated by the system utilizing an LED subset (some number of individual LED elements) of the LED array. One particular example, a one or a few LEDs (e.g., 1, 4, 9, etc.) may be lit up to form a bright or colored spot for the patient focus on. In such embodiments, the fixation target characteristic may be adjusted by the system controlling the LED array to change a color, intensity, or position of images made utilizing the LED subset.

In another embodiment, a monitor may be used as a fixation device with the fixation target being an image generated at the monitor (which may be a tiny monitor with a width of 1-3 inches, inclusive). In such implementations, the fixation target characteristic may be a color, intensity, or position of the image. In implementations including those with an LED array or a monitor, the fixation target may be an animated image. Examples of animated images are geometric images that change shape, pictures or figures generated by the LED elements that change or morph when different elements are activated, or other generally dynamic animations to keep hold the patient's attention and focus and reduce or eliminate any reflexive eye movement to refresh the image on the patient's retina. In one embodiment, the animated image may be a representation of the patient's facial expression, and the animation may be a change to the patient's facial expression. The facial expressions may be captured ahead of time by the system and replayed and changed during the treatment, or they may be based on a real-time image of the patient during the procedure. They could also consist of computerized caricatures (animated or still). Changes to the facial expression may include, for example, changing the shape of the mouth, the color of the patient's face, etc. In some implementations, the fixation target may be a still patient facial image. In some embodiments, correction of the tilt described previously may occur by moving the position of the fixation device rather than, or in addition to, any changes to the fixation target.

Figure 9:
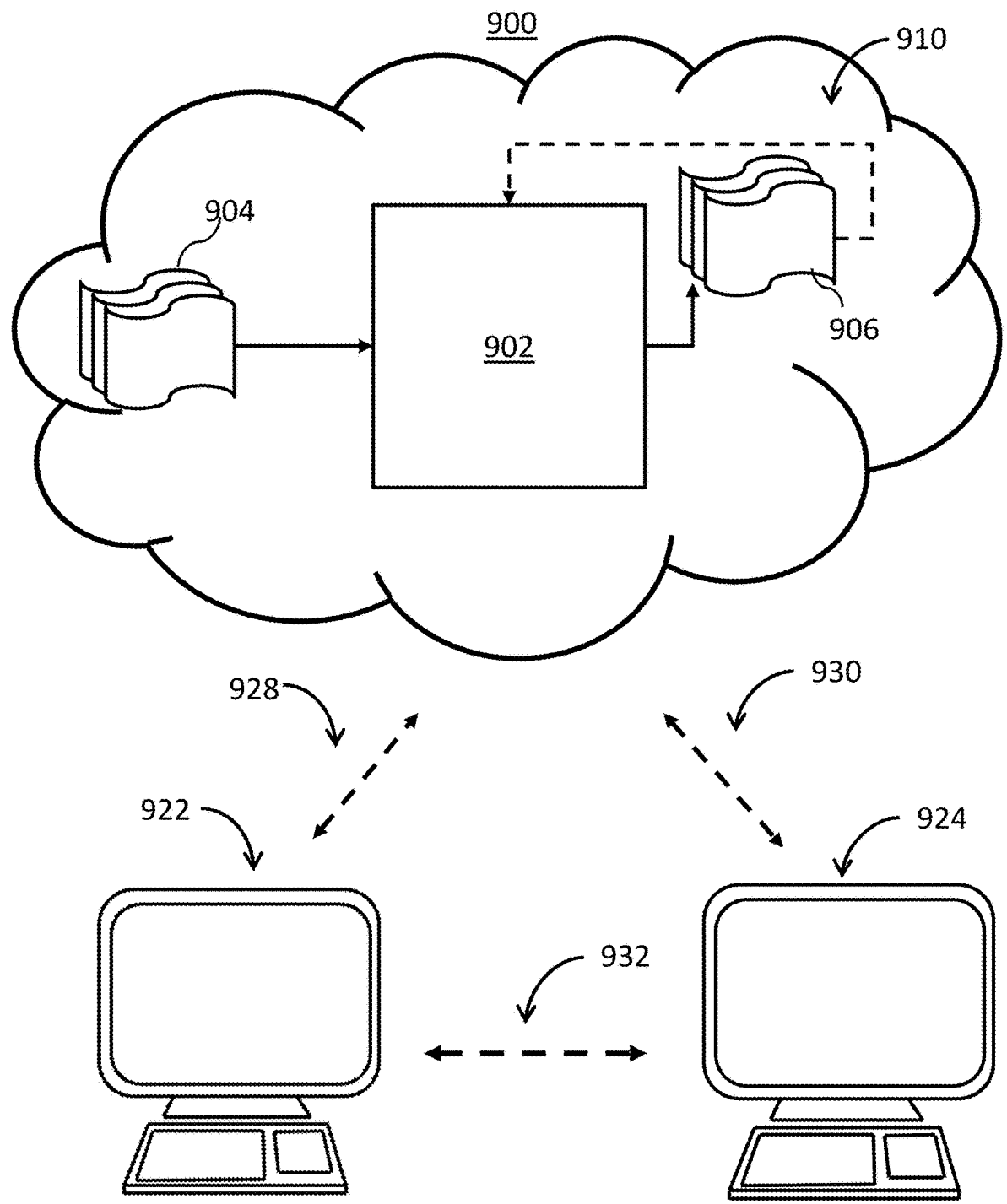
FIG. 9 shows an illustrative system for performing an eye color changing procedure in accordance with one or more embodiments.

FIG. 9 shows an illustrative system for performing an eye color changing procedure in accordance with one or more embodiments. For example, system 900 may represent the components used for performing an eye color changing procedure. For example, system 900 may power a local device to perform an eye color changing procedure where the required determination (e.g., iris mapping, pattern to follow, laser power to deliver, identification of patient, alignment of patient, etc.) are determined remotely and/or in the cloud. As shown in FIG. 9, system 900 may include user terminal 922 and user terminal 924. While shown as personal computers, in FIG. 9, it should be noted that user terminal 922 and user terminal 924 may be any computing device, including, but not limited to, a laptop computer, a tablet computer, a hand-held computer, other computer equipment (e.g., a server), including "smart," wireless, wearable, and/or mobile devices. FIG. 9 also includes cloud components 910. Cloud components 910 may alternatively be any computing device as described above and may include any type of mobile terminal, fixed terminal, or other device. For example, cloud components 910 may be implemented as a cloud computing system and may feature one or more component devices. It should also be noted that system 900 is not limited to three devices. Users may, for instance, utilize one or more other devices to interact with one another, one or more servers, or other components of system 900. It should be noted that, while one or more operations are described herein as being performed by particular components of system 900, those operations may, in some embodiments, be performed by other components of system 900. As an example, while one or more operations are described herein as being performed by components of user terminal 922, those operations may, in some embodiments, be performed by components of cloud components 910. In some embodiments, the various computers and systems described herein may include one or more computing devices that are programmed to perform the described functions. Additionally, or alternatively, multiple users may interact with system 900 and/or one or more components of system 900. For example, in one embodiment, a first user and a second user (e.g., a technician and a physician) may interact with system 900 using two different components.

With respect to the components of user terminal 922, user terminal 924, and cloud components 910, each of these devices may receive content and data via input/output (hereinafter "I/O") paths. Each of these devices may also include processors and/or control circuitry to send and receive commands, requests, and other suitable data using the I/O paths. The control circuitry may comprise any suitable processing circuitry. Each of these devices may also include a user input interface and/or user output interface (e.g., a display) for use in receiving and displaying data. For example, as shown in FIG. 9, both user terminal 922 and user terminal 924 include a display upon which to display data (e.g., information related to an eye color changing procedure).

Additionally, as user terminal 922 and user terminal 924 are shown as touchscreen smartphones, these displays also act as user input interfaces. It should be noted that in some embodiments, the devices may have neither user input interface nor displays and may instead receive and display content using another device (e.g., a dedicated display device such as a computer screen and/or a dedicated input device such as a remote control, mouse, voice input, etc.). Additionally, the devices in system 900 may run an application (or another suitable program). The application may cause the processors and/or control circuitry to perform operations related to an eye color changing procedure.

Each of these devices may also include electronic storages. The electronic storages may include non-transitory storage media that electronically stores information. The electronic storage media of the electronic storages may include one or both of (i) system storage that is provided integrally (e.g., substantially non-removable) with servers or client devices or (ii) removable storage that is removably connectable to the servers or client devices via, for example, a port (e.g., a USB port, a firewire port, etc.) or a drive (e.g., a disk drive, etc.). The electronic storages may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. The electronic storages may include one or more virtual storage resources (e.g., cloud storage, a virtual private network, and/or other virtual storage resources). The electronic storages may store software algorithms, information determined by the processors, information obtained from servers, information obtained from client devices, or other information that enables the functionality as described herein.

FIG. 9 also includes communication paths 928, 930, and 932. Communication paths 928, 930, and 932 may include the Internet, a mobile phone network, a mobile voice or data network (e.g., a 9G or LTE network), a cable network, a public switched telephone network, or other types of communications network or combinations of communications networks. Communication paths 928, 930, and 932 may separately or together include one or more communications paths, such as a satellite path, a fiber-optic path, a cable path, a path that supports Internet communications (e.g., IPTV), free-space connections (e.g., for broadcast or other wireless signals), or any other suitable wired or wireless communications path or combination of such paths. The computing devices may include additional communication paths linking a plurality of hardware, software, and/or firmware components operating together. For example, the computing devices may be implemented by a cloud of computing platforms operating together as the computing devices.

Cloud components 910 may be a database configured to store user data for a user. For example, the database may include user data that the system has collected about the user through prior operations and/or procedures. Alternatively, or additionally, the system may act as a clearing house for multiple sources of information about the user. Cloud components 910 may also include control circuitry configured to perform the various operations needed to perform an eye color changing procedure.

Cloud components 910 include machine learning model 902. Machine learning model 902 may take inputs 904 and provide outputs 906. The inputs may include multiple data sets such as a training data set and a test data set. Each of the plurality of data sets (e.g., inputs 904) may include data subsets related to user data, an eye color changing procedure, patient progress, and/or results. In some embodiments, outputs 906 may be fed back to machine learning model 902 as input to train machine learning model 902 (e.g., alone or in conjunction with user indications of the accuracy of outputs 906, labels associated with the inputs, or with other reference feedback information). In another embodiment, machine learning model 902 may update its configurations (e.g., weights, biases, or other parameters) based on the assessment of its prediction (e.g., outputs 906) and reference feedback information (e.g., indication of accuracy, results of procedure, reference labels, and/or other information). In another embodiment, where machine learning model 902 is a neural network, connection weights may be adjusted to reconcile differences between the neural network's prediction and the reference feedback. In a further use case, one or more neurons (or nodes) of the neural network may require that their respective errors are sent backward through the neural network to facilitate the update process (e.g., backpropagation of error). Updates to the connection weights may, for example, be reflective of the magnitude of error propagated backward after a forward pass has been completed. In this way, for example, the machine learning model 902 may be trained to generate better predictions (e.g., predictions related to an appropriate iris mapping to use, pattern to follow, laser power, level of eye color change, number of procedures, length of procedures, etc.

In some embodiments, machine learning model 902 may include an artificial neural network. In such embodiments, machine learning model 902 may include an input layer and one or more hidden layers. Each neural unit of machine learning model 902 may be connected with many other neural units of machine learning model 902. Such connections may be enforcing or inhibitory in their effect on the activation state of connected neural units. In some embodiments, each individual neural unit may have a summation function which combines the values of all of its inputs together. In some embodiments, each connection (or the neural unit itself) may have a threshold function such that the signal must surpass before it propagates to other neural units. Machine learning model 902 may be self-learning and trained, rather than explicitly programmed, and may perform significantly better in certain areas of problem solving, as compared to traditional computer programs. During training, an output layer of machine learning model 902 may correspond to a classification of machine learning model 902 and an input known to correspond to that classification may be input into an input layer of machine learning model 902 during training. During testing, an input without a known classification may be input into the input layer, and a determined classification may be output.

In some embodiments, machine learning model 902 may include multiple layers (e.g., where a signal path traverses from front layers to back layers). In some embodiments, back propagation techniques may be utilized by machine learning model 902 where forward stimulation is used to reset weights on the "front" neural units. In some embodiments, stimulation and inhibition for machine learning model 902 may be more free flowing, with connections interacting in a more chaotic and complex fashion. During testing, an output layer of machine learning model 902 may indicate whether or not a given input corresponds to a classification of machine learning model 902 (e.g., an eye color change requested, a pattern to follow, a laser power to deliver, alignment of patient, etc.).

Figure 10:
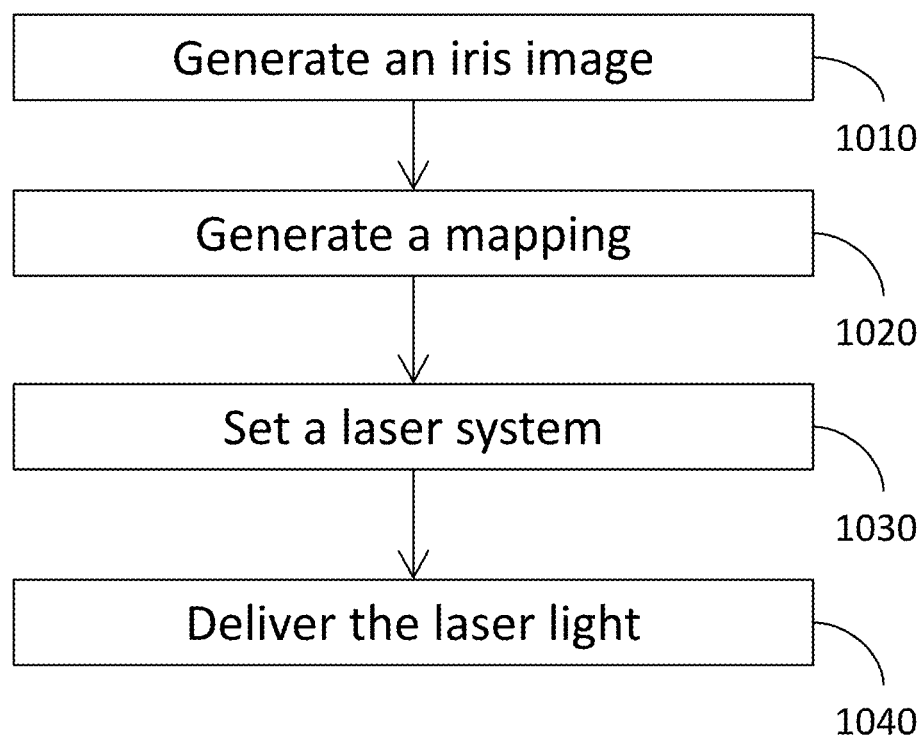
FIG. 10 shows steps for delivering laser light based on a mapping of the iris in accordance with one or more embodiments.

FIG. 10 shows steps for delivering laser light based on a mapping of the iris. For example, process 1000 (e.g., via one or more components of FIGS. 1-9) may represent the steps taken by one or more devices as shown in FIGS. 1-9 when performing an eye color alteration procedure.

At step 1010, process 1000 (e.g., via one or more components of FIGS. 1-9) generates an iris image. For example, the system may include an image sensor for imaging the iris prior to a color alteration procedure to generate an image of the iris. In some embodiments, the system may filter reflected light, from the stromal pigment to the image sensor, through a bandpass filter configured to pass a wavelength corresponding to the laser light.

At step 1020, process 1000 (e.g., via one or more components of FIGS. 1-9) generates a mapping. For example, the system may generate a mapping of the iris based on the imaging in step 1010. The mapping may include regions corresponding to varying absorption coefficients of a treatment wavelength in a stromal pigment of the iris. In some embodiments, the system may calculate absorption coefficients at the wavelength of the laser light in at least one of the regions. The system may also generate the mapping to be representative of at least one of the absorption coefficients and may include measuring the reflectivity of the image to determine the absorption coefficients, where the reflectivity of the image may be based on an inverse of a saturation in the image.

In some embodiments, the system may determine regions in the iris based upon the absorption coefficients in the regions. The system may deliver a set laser energy per pulse to the regions based on the absorption coefficients. In some embodiments, the process of determining the regions may include assigning pixels in the image to the regions based on the absorption coefficient at the pixels. The process may include the system accessing a laser energy lookup table to obtain the set laser energy, with the laser energy lookup table comprising ranges of absorption coefficients and corresponding laser energies. In some embodiments, there may be three ranges of absorption coefficients, wherein a first absorption coefficient corresponds to a laser power of approximately 34 times a maximum permissible exposure, a second absorption coefficient corresponds to a laser energy of approximately 63 times a maximum permissible exposure, and a third absorption coefficient corresponds to a laser energy of approximately 84 times a maximum permissible exposure.

At step 1030, process 1000 (e.g., via one or more components of FIGS. 1-9) sets a laser system. For example, the system may set, based on the mapping, a laser system to deliver laser light at a first laser power to a location in an eye of the patient. The first laser power may be sufficient to cause elimination of at least a portion of stromal pigment in the iris.

At step 1040, process 1000 (e.g., via one or more components of FIGS. 1-9) delivers the laser light. For example, the system may include a laser system and use the laser system to deliver the laser light (e.g., as described above in FIGS. 2-4).

Figure 11:
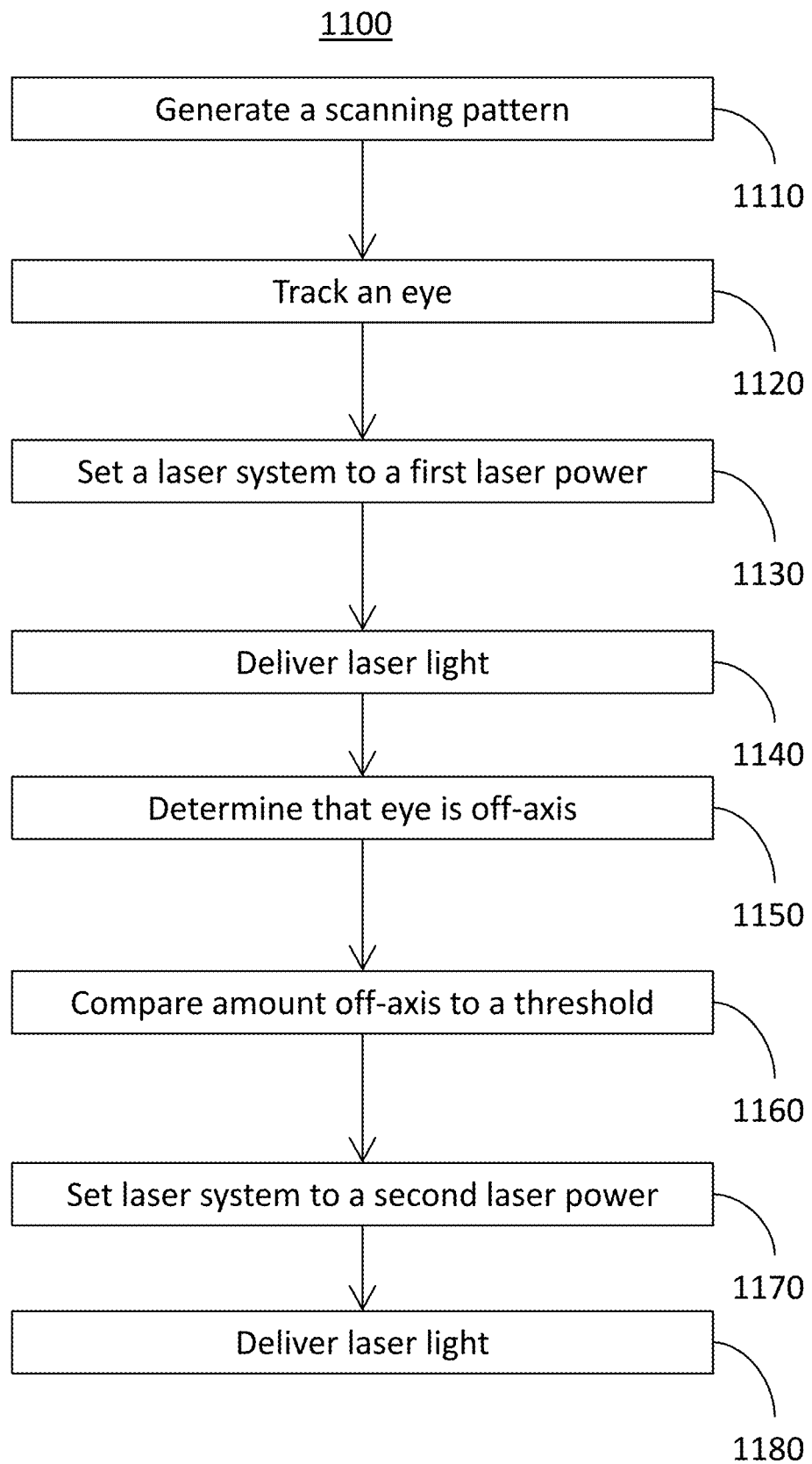
FIG. 11 shows steps for delivering laser light that includes determining an amount the eye is off axis.

FIG. 11 shows steps for delivering laser light that includes determining an amount the eye is off axis. For example, process 1100 (e.g., via one or more components of FIGS. 1-9) may represent the steps taken by one or more devices as shown in FIGS. 1-9 when performing an eye color alteration procedure.

At step 1110, process 1100 (e.g., via one or more components of FIGS. 1-9) e generates a scanning pattern. For example, the system may deliver laser power to at least 50% of the anterior surface of an iris of the patient during the color alteration procedure. In some embodiments, an image sensor may image the iris prior to the color alteration procedure to generate an image of the iris. The process may include performing boundary detection on the image to determine a pupil boundary and a limbus boundary. The process may also include generating the scanning pattern to cover at least 50% of the anterior surface of the iris based on a laser spot size. In some embodiments, the process may include generating the scanning pattern to be a spiral pattern extending from approximately the pupil boundary to approximately the limbus boundary.

At step 1120, process 1100 (e.g., via one or more components of FIGS. 1-9) tracks an eye. For example, the system may include an optical tracking system tracking an axial alignment of an eye of the patient during the color alteration procedure.

At step 1130, process 1100 (e.g., via one or more components of FIGS. 1-9) sets a laser system to deliver a first laser power. For example, the system may deliver the first laser power to a location in the eye of the patient. The first laser power may be sufficient to cause elimination of at least a portion of stromal pigment in an iris of the eye.

At step 1140, process 1100 (e.g., via one or more components of FIGS. 1-9) delivers laser light. For example, the system may include the laser system for delivering the laser light. For example, the delivery by the system may be according to the scanning pattern, and the laser light may be at the eye and at the first laser power.

At step 1150, process 1100 (e.g., via one or more components of FIGS. 1-9) determines that the eye is off axis. For example, the system may determine an amount based on the axial alignment of the eye.

At step 1160, process 1100 (e.g., via one or more components of FIGS. 1-9) compares the amount to a first threshold amount. For example, the threshold amount may be determined based on a user-specific, procedure-specific, and/or industry standard. The system may retrieve this threshold prior to the procedure and may iteratively compare a detected amount to the threshold. For example, the system may compare the amount to the threshold amount using one or more quantitative or qualitative metrics. These metrics may include minimum and/or maximum amounts as well as preferred ranges and/or procedure boundaries. In some embodiments, the threshold may be set based on one or more safety protocols. For example, the system may determine an amount that effects, or upon which a determination of MPE for the procedure was based, and set a threshold based on that amount.

In some embodiments, the process may include the system comparing the amount to a second threshold amount, where the second threshold amount may be less than the first threshold amount. The laser system may be controlled to move the laser light in a horizontal plane while keeping the laser light substantially perpendicular to the iris and while maintaining delivery of the laser light to the eye at the first laser power. In some embodiments, the second threshold amount may be approximately 100 µm.

At step 1170, process 1100 (e.g., via one or more components of FIGS. 1-9) sets the laser system to a second laser power. For example, the setting may be based on the system determining that the amount equals or exceeds the first threshold amount, wherein the second laser power is less than the first laser power. In some embodiments, the second laser power may be insufficient to cause elimination of at least the portion of the stromal pigment. In some embodiments, the first threshold amount may be approximately 500 µm. In some embodiments, the process, in response to determining that the amount does not equal or exceed the first threshold amount, may maintain the delivery of the laser light to the eye at the first laser power.

At step 1180, process 1100 (e.g., via one or more components of FIGS. 1-9) delivers the laser light. For example, the system may include a laser system delivering laser light. For example, the system may deliver laser light to the eye at the second laser power according to the scanning pattern. In some embodiments, the process may include adjusting a delivery angle of the laser system to compensate for the amount.

Figure 12:
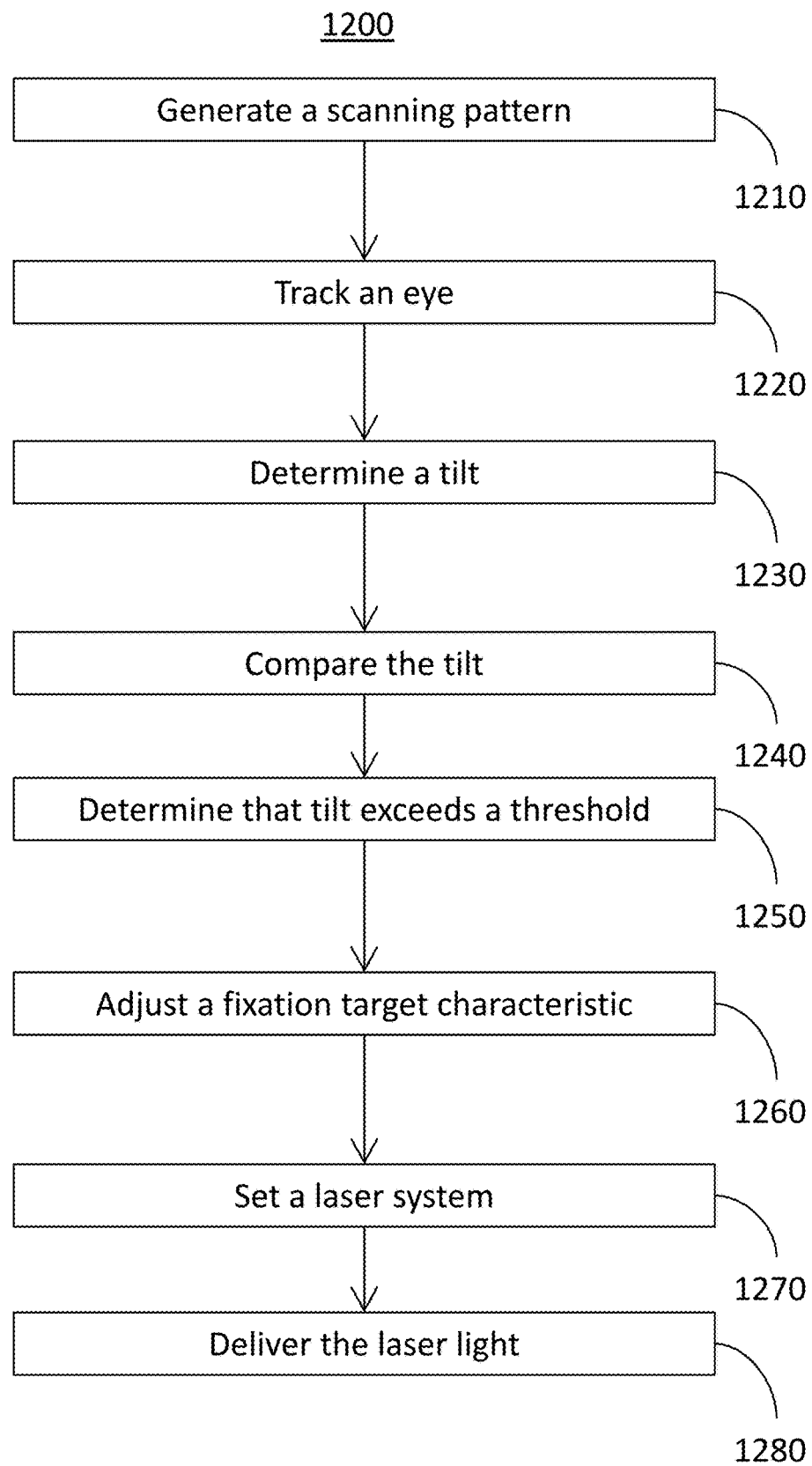
FIG. 12 shows steps for delivering laser light that includes compensating for a determined tilt of the iris.

FIG. 12 shows steps for delivering laser light that includes compensating for a determined tilt of the iris. For example, process 1200 (e.g., via one or more components of FIGS. 1-9) may represent the steps taken by one or more devices as shown in FIGS. 1-9 when performing an eye color alteration procedure.

At step 1210, process 1200 (e.g., via one or more components of FIGS. 1-9) generates a scanning pattern. For example, the scanning pattern may be for the delivery of laser power to at least 50% of an anterior surface of an iris of the patient during the color alteration procedure.

At step 1220, process 1200 (e.g., via one or more components of FIGS. 1-9) tracks an eye. For example, a rangefinder may be used for tracking the eye of the patient during the color alteration procedure.

At step 1230, process 1200 (e.g., via one or more components of FIGS. 1-9) determines a tilt of the eye. For example, the rangefinder that is part of an optical tracking system may be utilized to determine an amount of tilt of the iris based on the optical tracking system interpreting optical data received at the optical tracking system from the eye of the patient. In other embodiments, the process may also include the system determining of the tilt by measuring a distance from a reference point to at least three points on the iris to determine a plane of the iris. In yet other embodiments, the process may include the system determining of the tilt further by measuring a distance from a reference point to at least four points on the iris to determine a plane of the iris. In some embodiments, the process may include the system determining the tilt by generating a Purkinje image on a cornea of the eye, determining a boundary of a pupil of the eye, and determining the tilt from a position of the Purkinje image and the boundary.

At step 1240, process 1200 (e.g., via one or more components of FIGS. 1-9) compares the amount to a threshold amount. For example, the threshold amount may be determined based on a user-specific, procedure-specific, and/or industry standard. The system may retrieve this threshold prior to the procedure and may iteratively compare a detected amount to the threshold.

At step 1250, process 1200 (e.g., via one or more components of FIGS. 1-9) determines that the amount equals or exceeds the threshold amount. For example, the system may compare the amount to the threshold amount using one or more quantitative or qualitative metrics. These metrics may include minimum and/or maximum amounts of allowable tilt as well as preferred ranges and/or procedure boundaries. In some embodiments, the threshold may be set based on one or more safety protocols. For example, the system may determine an amount of tilt that effects, or upon which a determination of MPE for the procedure was based, and set a threshold based on that amount.

At step 1260, process 1200 (e.g., via one or more components of FIGS. 1-9) adjusts a fixation target characteristic. For example, the adjustment of the fixation target may compensate for the amount of tilt. In some embodiments, the fixation target characteristic may include an appearance and/or a position of the fixation target. In some embodiments, the fixation target may include colors that are different from a color of the laser light. In some embodiments, the process may include generating the fixation target utilizing an LED subset of an LED array and adjusting the fixation target characteristic by controlling the LED array to change a color, intensity, or position of images of the LED subset. In some embodiments, the fixation target may be an image on a monitor and the fixation target characteristic may be a color, intensity, or a position of the image comprising the fixation target generated at the monitor. In some embodiments, the fixation target may be an animated image, and wherein the fixation target characteristic is animation. The animation may be of a change to a patient facial expression.

At step 1270, process 1200 (e.g., via one or more components of FIGS. 1-9) sets a laser system. For example, the system may deliver laser light having a laser power that will cause elimination of at least a portion of stromal pigment of the iris.

At step 1280, process 1200 (e.g., via one or more components of FIGS. 1-9) delivers the laser light. For example, the system may include a laser system for delivering laser light. For example, the laser light may be delivered by the system at a first laser power and according to the scanning pattern. The first laser power may be sufficient to cause elimination of at least a portion of stromal pigment of the iris.

The above-described embodiments of the present disclosure are presented for purposes of illustration and not of limitation, and the present disclosure is limited only by the claims which follow. Furthermore, it should be noted that the features and limitations described in any one embodiment may be applied to any other embodiment herein, and flowcharts or examples relating to one embodiment may be combined with any other embodiment in a suitable manner, done in different orders, or done in parallel. In addition, the systems and methods described herein may be performed in real time. It should also be noted that the systems and/or methods described above may be applied to, or used in accordance with, other systems and/or methods.

The present techniques will be better understood with reference to the following enumerated embodiments:

Embodiment 1: A method for altering an eye color of a patient with a color alteration procedure, the method comprising: imaging an iris with an image sensor prior to the color alteration procedure to generate an image of the iris; generating, based on the image, a mapping of the iris, the mapping comprising a plurality of regions corresponding to varying absorption coefficients of a treatment wavelength in a stromal pigment of the iris; setting, based on the mapping, a laser system to deliver laser light at a first laser power to a location in an eye of the patient, wherein the first laser power is sufficient to cause elimination of at least a portion of stromal pigment in the iris; and delivering the laser light with the laser system.

Embodiment 2: The method of any of the preceding embodiments, the generating of the mapping further comprising: calculating absorption coefficients at the wavelength of the laser light in at least one of the plurality of regions; and generating the mapping to be representative of at least one of the absorption coefficients.

Embodiment 3: The method of any of the preceding embodiments, the calculating comprising measuring the reflectivity of the image to determine the absorption coefficients.

Embodiment 4: The method of any of the preceding embodiments, wherein the reflectivity of the image is based on an inverse of a saturation in the image.

Embodiment 5: The method of any of the preceding embodiments, the imaging further comprising: filtering reflected light, from the stromal pigment to the image sensor, through a bandpass filter configured to pass a wavelength corresponding to the laser light.

Embodiment 6: The method of any of the preceding embodiments, further comprising: determining regions in the iris based upon the absorption coefficients in the regions; and delivering a set laser energy per pulse to the regions based on the absorption coefficients.

Embodiment 7: The method of any of the preceding embodiments, the determining of the regions further comprising assigning pixels in the image to the regions based on the absorption coefficient at the pixels.

Embodiment 8: The method of any of the preceding embodiments, further comprising accessing a laser energy lookup table to obtain the set laser energy, the laser energy lookup table comprising ranges of absorption coefficients and corresponding laser energies.

Embodiment 9: The method of any of the preceding embodiments, wherein there are three ranges of absorption coefficients and a first absorption coefficient corresponds to a laser power of approximately 34 times a maximum permissible exposure, a second absorption coefficient corresponds to a laser energy of approximately 63 times a maximum permissible exposure, and a third absorption coefficient corresponds to a laser energy of approximately 84 times a maximum permissible exposure.

Embodiment 10: A method for altering an eye color of a patient with a color alteration procedure, the method comprising: generating a scanning pattern for the delivery of laser power to at least 50% of an anterior surface of an iris of the patient during the color alteration procedure; tracking, with an optical tracking system, an axial alignment of an eye of the patient during the color alteration procedure; setting a laser system to deliver a first laser power to a location in the eye of the patient, wherein the first laser power is sufficient to cause elimination of at least a portion of stromal pigment in an iris of the eye; delivering, with the laser system and according to the scanning pattern, laser light to the eye at the first laser power; determining an amount that the eye is off axis based on the axial alignment; comparing the amount to a first threshold amount; setting the laser system to a second laser power based on determining that the amount equals or exceeds the first threshold amount, wherein the second laser power is less than the first laser power; and delivering, with the laser system and according to the scanning pattern, laser light to the eye at the second laser power.

Embodiment 11: The method of any of the preceding embodiments, the generating of the scanning pattern comprising: imaging an iris with an image sensor prior to the color alteration procedure to generate an image of the iris; performing boundary detection on the image to determine a pupil boundary and a limbus boundary; and generating the scanning pattern to cover at least 50% of the anterior surface of the iris based on a laser spot size.

Embodiment 12: The method of any of the preceding embodiments, further comprising generating the scanning pattern to be a spiral pattern extending from approximately the pupil boundary to approximately the limbus boundary.

Embodiment 13: The method of any of the preceding embodiments, wherein the second laser power is insufficient to cause elimination of at least the portion of the stromal pigment.

Embodiment 14: The method of any of the preceding embodiments, wherein the first threshold amount is approximately 500 μm.

Embodiment 15: The method of any of the preceding embodiments, further comprising: in response to determining that the amount does not equal or exceed the first threshold amount, maintaining the delivery of the laser light to the eye at the first laser power.

Embodiment 16: The method of any of the preceding embodiments, further comprising: comparing the amount to a second threshold amount, wherein the second threshold amount is less than the first threshold amount; and controlling the laser system to move the laser light in a horizontal plane while keeping the laser light substantially perpendicular to the iris and while maintaining delivery of the laser light to the eye at the first laser power.

Embodiment 17: The method of any of the preceding embodiments, wherein the second threshold amount is approximately 100 μm.

Embodiment 18: The method of any of the preceding embodiments, further comprising adjusting a delivery angle of the laser system to compensate for the amount.

Embodiment 19: A method for altering an eye color of a patient with a color alteration procedure, the method comprising: generating a scanning pattern for the delivery of laser power to at least 50% of an anterior surface of an iris of the patient during the color alteration procedure; tracking, with a rangefinder, an eye of the patient during the color alteration procedure; determining, with the rangefinder, that is part of an optical tracking system, an amount of tilt of an iris based on the optical tracking system interpreting optical data received at the optical tracking system from the eye of the patient; comparing the amount to a threshold amount; determining that the amount equals or exceeds the threshold amount; adjusting a fixation target characteristic of a fixation target to compensate for the amount; setting a laser system to deliver laser light having a laser power that will cause elimination of at least a portion of stromal pigment of the iris; and delivering, with the laser system and according to the scanning pattern, laser light having a first laser power, wherein the first laser power causes elimination of at least a portion of stromal pigment of the iris.

Embodiment 20: The method of any of the preceding embodiments, wherein the fixation target characteristic comprises an appearance and/or a position of the fixation target.

Embodiment 21: The method of any of the preceding embodiments, the determining of the tilt further comprising measuring a distance from a reference point to at least three points on the iris to determine a plane of the iris.

Embodiment 22: The method of any of the preceding embodiments, the determining of the tilt further comprising measuring a distance from a reference point to at least four points on the iris to determine a plane of the iris.

Embodiment 23: The method of any of the preceding embodiments, wherein the determination of the tilt comprises: generating a Purkinje image on a cornea of the eye; determining a boundary of a pupil of the eye; and determining the tilt from a position of the Purkinje image and the boundary.

Embodiment 24: The method of any of the preceding embodiments, wherein the fixation target includes colors that are different from a color of the laser light.

Embodiment 25: The method of any of the preceding embodiments, further comprising: generating the fixation target utilizing an LED subset of an LED array; and adjusting the fixation target characteristic by controlling the LED array to change a color, intensity, or position of images of the LED subset.

Embodiment 26: The method of any of the preceding embodiments, wherein the fixation target is an image on a monitor, and wherein the fixation target characteristic is a color, intensity, or a position of the image comprising the fixation target generated at the monitor.

Embodiment 27: The method of any of the preceding embodiments, wherein the fixation target is an animated image, and wherein the fixation target characteristic is animation.

Embodiment 28: The method of any of the preceding embodiments, wherein the animation is of a change to a patient facial expression.

Embodiment 29: The method of any of the preceding embodiments, wherein the fixation target is of a still patient facial image.

Embodiment 30: A method for altering an eye color of a patient with a color alteration procedure, the method comprising: generating a scanning pattern for the delivery of laser power to at least 50% of an anterior surface of an iris of the patient during the color alteration procedure; tracking, with an optical tracking system, an eye of the patient during the color alteration procedure; determining, with a temperature sensor, a temperature of at least a portion of an iris of the eye that contains stromal pigment, wherein the temperature sensor is non-invasive to the iris; setting a laser system to deliver laser light at a laser power that does not cause the temperature to exceed 140 degrees during the color alteration procedure; and delivering the laser light with the laser system according to the scanning pattern.

Embodiment 31: The method of any of the preceding embodiments, wherein the temperature sensor is an infrared imaging system, the method further comprising converting received infrared radiation from the eye to the temperature.

Embodiment 32: The method of any of the preceding embodiments, wherein infrared wavelengths detected by the infrared imaging system are between 1100 and 1200 nm.

A tangible, non-transitory, machine-readable medium storing instructions that, when executed by a data processing apparatus, cause the data processing apparatus to perform operations comprising those of any of the above method embodiments 1-32.

A system comprising: one or more processors; and memory storing instructions that, when executed by the processors, cause the processors to effectuate operations comprising those of any of the above method embodiments 1-32.

APPENDIX 1

Thermal hazard weighting functions

| Wavelength (nm) | Thermal hazard weighting function $R(\lambda)$ |
|---|---|
| 305 | 2.19 |
| 310 | 2.31 |
| 315 | 2.42 |
| 320 | 2.53 |
| 325 | 2.63 |
| 330 | 2.72 |
| 335 | 2.80 |
| 340 | 2.87 |
| 345 | 2.94 |
| 350 | 2.99 |
| 355 | 3.04 |
| 360 | 3.08 |
| 365 | 3.11 |
| 370 | 3.14 |
| 375 | 3.16 |
| 380 | 3.17 |
| 385 | 3.17 |
| 390 | 3.17 |
| 395 | 3.17 |
| 400 | 3.16 |
| 405 | 3.14 |
| 410 | 3.12 |
| 415 | 3.10 |
| 420 | 3.07 |
| 425 | 3.04 |
| 430 | 3.01 |
| 435 | 2.97 |
| 440 | 2.93 |
| 445 | 2.89 |
| 450 | 2.85 |
| 455 | 2.81 |
| 460 | 2.76 |
| 465 | 2.72 |
| 470 | 2.67 |
| 475 | 2.63 |
| 480 | 2.58 |
| 485 | 2.53 |
| 490 | 2.48 |
| 495 | 2.44 |
| 500 | 2.39 |
| 505 | 2.34 |
| 510 | 2.30 |
| 515 | 2.25 |
| 520 | 2.20 |
| 525 | 2.16 |
| 530 | 2.11 |
| 535 | 2.07 |
| 540 | 2.03 |
| 545 | 1.98 |
| 550 | 1.94 |
| 555 | 1.90 |
| 560 | 1.86 |
| 565 | 1.82 |
| 570 | 1.78 |
| 575 | 1.74 |
| 580 | 1.70 |
| 585 | 1.66 |
| 590 | 1.63 |
| 595 | 1.59 |
| 600 | 1.55 |
| 605 | 1.52 |
| 610 | 1.49 |
| 615 | 1.45 |
| 620 | 1.42 |
| 625 | 1.39 |
| 630 | 1.36 |
| 635 | 1.33 |
| 640 | 1.30 |
| 645 | 1.27 |
| 650 | 1.24 |
| 655 | 1.22 |
| 660 | 1.19 |
| 665 | 1.16 |
| 670 | 1.14 |
| 675 | 1.11 |
| 680 | 1.09 |
| 685 | 1.07 |
| 690 | 1.04 |
| 695 | 1.02 |
| 700 | 1.00 |
| 705 | 0.98 |
| 710 | 0.96 |
| 715 | 0.94 |
| 720 | 0.92 |
| 725 | 0.90 |
| 730 | 0.88 |
| 735 | 0.86 |
| 740 | 0.84 |
| 745 | 0.83 |
| 750 | 0.81 |
| 755 | 0.79 |
| 760 | 0.78 |
| 765 | 0.76 |
| 770 | 0.74 |
| 775 | 0.73 |
| 780 | 0.71 |
| 785 | 0.70 |
| 790 | 0.69 |
| 795 | 0.67 |
| 800 | 0.66 |
| 805 | 0.65 |
| 810 | 0.63 |
| 815 | 0.62 |
| 820 | 0.61 |
| 825 | 0.60 |
| 830 | 0.59 |
| 835 | 0.57 |
| 840 | 0.56 |
| 845 | 0.55 |
| 850 | 0.54 |
| 855 | 0.53 |
| 860 | 0.51 |
| 865 | 0.50 |
| 870 | 0.49 |
| 875 | 0.47 |
| 880 | 0.47 |
| 885 | 0.46 |
| 890 | 0.44 |
| 895 | 0.43 |
| 900 | 0.42 |
| 905 | 0.41 |
| 910 | 0.40 |
| 915 | 0.38 |
| 920 | 0.35 |
| 925 | 0.32 |
| 930 | 0.29 |
| 935 | 0.26 |
| 940 | 0.23 |
| 945 | 0.19 |
| 950 | 0.16 |
| 955 | 0.15 |
| 960 | 0.15 |
| 965 | 0.14 |

APPENDIX 1-continued

Thermal hazard weighting functions

| Wavelength (nm) | Thermal hazard weighting function R(λ) |
|---|---|
| 970 | 0.13 |
| 975 | 0.13 |
| 980 | 0.13 |
| 985 | 0.13 |
| 990 | 0.13 |
| 995 | 0.14 |
| 1000 | 0.15 |
| 1005 | 0.15 |
| 1010 | 0.16 |
| 1015 | 0.16 |
| 1020 | 0.17 |
| 1025 | 0.18 |
| 1030 | 0.19 |
| 1035 | 0.20 |
| 1040 | 0.21 |
| 1045 | 0.21 |
| 1050 | 0.22 |
| 1055 | 0.22 |
| 1060 | 0.21 |
| 1065 | 0.21 |
| 1070 | 0.20 |
| 1075 | 0.20 |
| 1080 | 0.20 |
| 1085 | 0.20 |
| 1090 | 0.20 |
| 1095 | 0.19 |
| 1100 | 0.17 |
| 1105 | 0.14 |
| 1110 | 0.11 |
| 1115 | 0.084 |
| 1120 | 0.068 |
| 1125 | 0.059 |
| 1130 | 0.054 |
| 1135 | 0.050 |
| 1140 | 0.046 |
| 1145 | 0.040 |
| 1150 | 0.034 |
| 1155 | 0.029 |
| 1160 | 0.025 |
| 1165 | 0.021 |
| 1170 | 0.019 |
| 1175 | 0.017 |
| 1180 | 0.016 |
| 1185 | 0.016 |
| 1190 | 0.015 |
| 1195 | 0.015 |
| 1200 | 0.015 |
| 1205 | 0.016 |
| 1210 | 0.016 |
| 1215 | 0.017 |
| 1220 | 0.018 |
| 1225 | 0.019 |
| 1230 | 0.019 |
| 1235 | 0.020 |
| 1240 | 0.020 |
| 1245 | 0.020 |
| 1250 | 0.020 |
| 1255 | 0.019 |
| 1260 | 0.019 |
| 1265 | 0.018 |
| 1270 | 0.017 |
| 1275 | 0.015 |
| 1280 | 0.014 |
| 1285 | 0.013 |
| 1290 | 0.012 |
| 1295 | 0.011 |
| 1300 | 0.010 |
| 1305 | 0.009 |
| 1310 | 0.007 |
| 1315 | 0.006 |
| 1320 | 0.005 |
| 1325 | 0.004 |
| 1330 | 0.003 |
| 1335 | 0.002 |
| 1340 | 0.002 |
| 1345 | 0.001 |
| 1350 | 0.001 |

What is claimed is:

1. A method for altering an eye color of a patient with a color alteration procedure, the method comprising:
   generating a scanning pattern for delivery of laser power to at least 50% of an anterior surface of an iris of the patient during the color alteration procedure;
   tracking, with a rangefinder that is part of an optical tracking system, an eye of the patient during the color alteration procedure;
   determining, with the rangefinder, an amount of tilt of an iris based on the optical tracking system interpreting optical data received at the optical tracking system from the eye of the patient;
   comparing the amount to a threshold amount;
   determining that the amount equals or exceeds the threshold amount;
   adjusting a fixation target characteristic of a fixation target to compensate for the amount;
   setting a laser system to deliver laser light having a laser power that will cause elimination of at least a portion of stromal pigment of the iris; and
   delivering, with the laser system and according to the scanning pattern, laser light having a first laser power, wherein the first laser power causes elimination of at least a portion of stromal pigment of the iris.

2. An apparatus for altering an eye color of a patient with a color alteration procedure, the apparatus comprising an optical tracking system having a rangefinder, a laser system, and a control system configured to:
   generate a scanning pattern for delivery of laser power to at least 50% of an anterior surface of an iris of the patient during the color alteration procedure;
   track an eye of the patient during the color alteration procedure using the rangefinder;
   determine, with the rangefinder, an amount of tilt of an iris based on the optical tracking system interpreting optical data received at the optical tracking system from the eye of the patient;
   compare the amount to a threshold amount;
   determine that the amount equals or exceeds the threshold amount;
   adjust a fixation target characteristic of a fixation target to compensate for the amount;
   set the laser system to deliver laser light having a laser power that will cause elimination of at least a portion of stromal pigment of the iris; and
   deliver, with the laser system and according to the scanning pattern, laser light having a first laser power, wherein the first laser power causes elimination of at least a portion of stromal pigment of the iris.

3. The apparatus of claim 2 further comprising:
an image sensor for imaging the iris prior to the color alteration procedure to generate an image of the iris, the control system being configured to:
perform boundary detection on the image to determine a pupil boundary and a limbus boundary; and
generate the scanning pattern to cover at least 50% of the anterior surface of the iris based on a laser spot size.

4. The apparatus of claim 2, wherein the control system is further configured to:
determining, with a temperature sensor, a temperature of at least a portion of the eye that contains stromal pigment, wherein the temperature sensor is non-invasive to the iris; and
delivering the laser light having a second laser power.

5. The apparatus of claim 2, wherein the fixation target characteristic comprises an appearance and/or a position of the fixation target.

6. The apparatus of claim 2, wherein determining the amount of the tilt further comprises measuring a distance from a reference point to at least three points on the iris to determine a plane of the iris.

7. The apparatus of claim 2, wherein determining the amount of the tilt further comprises:
generating a Purkinje image on a cornea of the eye;
determining a boundary of a pupil of the eye; and
determining the tilt from a position of the Purkinje image and the boundary.

8. The apparatus of claim 2, wherein the fixation target includes colors that are different from a color of the laser light.

9. The apparatus of claim 2, wherein the control system is further configured to:
generate the fixation target utilizing an LED subset of an LED array; and
adjust the fixation target characteristic by controlling the LED array to change a color, intensity, or position of images of the LED subset.

10. The apparatus of claim 2, wherein the fixation target is an image on a monitor, and wherein the fixation target characteristic is a color, intensity, or a position of the image comprising the fixation target generated at the monitor.

11. The apparatus of claim 2, wherein the fixation target is an animated image, and wherein the fixation target characteristic is animation.

12. The apparatus of claim 11, wherein the animation is of a change to a patient facial expression.

13. A non-transitory, computer readable medium comprising instructions recorded thereon that when executed by one or more processors causes operations comprising:
generating a scanning pattern for delivery of laser power to at least 50% of an anterior surface of an iris;
tracking, with a rangefinder that is part of an optical tracking system, an eye;
determining, with the rangefinder, an amount of tilt of an iris based on the optical tracking system interpreting optical data received at the optical tracking system from the eye;
comparing the amount to a threshold amount;
determining that the amount equals or exceeds the threshold amount;
adjusting a fixation target characteristic of a fixation target to compensate for the amount;
setting a laser system to deliver laser light; and
delivering, with the laser system and according to the scanning pattern, laser light having a first laser power, wherein the first laser power causes an effect on iris tissue.

14. The non-transitory, computer readable medium of claim 13, wherein the fixation target characteristic comprises an appearance and/or a position of the fixation target.

15. The non-transitory, computer readable medium of claim 14, wherein the fixation target is an animated image, and wherein the fixation target characteristic is animation.

16. The non-transitory, computer readable medium of claim 15, wherein the animation is of a facial expression.

17. The non-transitory, computer readable medium of claim 16, wherein the instructions further cause operations comprising:
determining, with a temperature sensor, a temperature of at least a portion of the eye that contains stromal pigment, wherein the temperature sensor is non-invasive to the iris; and
delivering the laser light having a second laser power.

18. The non-transitory, computer readable medium of claim 13, wherein determining the amount of the tilt further comprising measuring a distance from a reference point to at least three points on the iris to determine a plane of the iris.

19. The non-transitory, computer readable medium of claim 13, wherein determining the amount of the tilt comprises:
generating a Purkinje image on a cornea of the eye;
determining a boundary of a pupil of the eye; and
determining the tilt from a position of the Purkinje image and the boundary.

20. The non-transitory, computer readable medium of claim 13, wherein the fixation target includes colors that are different from a color of the laser light.

21. The non-transitory, computer readable medium of claim 13, wherein the instructions further cause operations comprising:
generating the fixation target utilizing an LED subset of an LED array; and
adjusting the fixation target characteristic by controlling the LED array to change a color, intensity, or position of images of the LED subset.

22. The non-transitory, computer readable medium of claim 13, wherein the fixation target is an image on a monitor, and wherein the fixation target characteristic is a color, intensity, or a position of the image comprising the fixation target generated at the monitor.

* * * * *